(12) United States Patent
Devengenzo et al.

(10) Patent No.: US 12,016,647 B2
(45) Date of Patent: Jun. 25, 2024

(54) SURGICAL DRAPE AND SYSTEMS INCLUDING SURGICAL DRAPE AND ATTACHMENT SENSOR

(71) Applicant: INTUITIVE SURGICAL OPERATIONS, INC., Sunnyvale, CA (US)

(72) Inventors: Roman L. Devengenzo, San Jose, CA (US); Michael L. Hanuschik, Mountain View, CA (US); Gerard J. Labonville, San Jose, CA (US); Paul W. Mohr, Mountain View, CA (US); Tyler J. Morrissette, Niantic, CT (US); Joseph P. Orban, III, Norwalk, CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 640 days.

(21) Appl. No.: 17/178,776

(22) Filed: Feb. 18, 2021

(65) Prior Publication Data

US 2021/0267703 A1 Sep. 2, 2021

Related U.S. Application Data

(63) Continuation of application No. 15/126,727, filed as application No. PCT/US2015/020929 on Mar. 17, 2015, now Pat. No. 10,932,877.
(Continued)

(51) Int. Cl.
*A61B 46/10* (2016.01)
*A61B 34/30* (2016.01)
(Continued)

(52) U.S. Cl.
CPC .............. *A61B 46/10* (2016.02); *A61B 34/30* (2016.02); *A61B 34/35* (2016.02); *A61B 46/23* (2016.02);
(Continued)

(58) Field of Classification Search
CPC ......... A61B 46/10; A61B 46/23; A61B 34/35; A61B 34/30; A61B 50/00; A61B 50/30;
(Continued)

(56) References Cited

U.S. PATENT DOCUMENTS 3,483,494 A 12/1969 Harry
5,080,108 A 1/1992 Roth
(Continued)

FOREIGN PATENT DOCUMENTS

BE 853518 A 8/1977
BE 1018961 A4 11/2011
(Continued)

OTHER PUBLICATIONS

Extended European Search Report for Application No. EP22160050.5, dated Jul. 29, 2022, 05 pages.
(Continued)

*Primary Examiner* — Camtu T Nguyen
(74) *Attorney, Agent, or Firm* — JONES ROBB, PLLC

(57) ABSTRACT

A surgical drape for a patient side cart of a teleoperated surgical system may comprise a body sized and shaped to cover at least a portion of an arm or main column of the patient side cart, and an attachment device feature connected to the body, the attachment device feature being configured to install the surgical drape to the arm or main column so as to cover at least a portion of the arm or main column with the surgical drape. In an installed position of the surgical drape on the arm or the main column, the attachment device
(Continued)

feature is positioned at a location in sensing proximity of a sensor of the patient side cart.

10 Claims, 17 Drawing Sheets

Related U.S. Application Data

(60) Provisional application No. 61/954,187, filed on Mar. 17, 2014.

(51) Int. Cl.
| | |
|---|---|
| *A61B 34/35* | (2016.01) |
| *A61B 46/23* | (2016.01) |
| *A61B 50/00* | (2016.01) |
| *A61B 50/20* | (2016.01) |
| *A61B 50/30* | (2016.01) |
| *A61B 90/50* | (2016.01) |
| *A61B 17/00* | (2006.01) |

(52) U.S. Cl.
CPC .............. *A61B 50/00* (2016.02); *A61B 50/20* (2016.02); *A61B 50/30* (2016.02); *A61B 90/50* (2016.02); *A61B 2017/00477* (2013.01)

(58) Field of Classification Search
CPC .................... A61B 90/50; A61B 90/20; A61B 2017/00477
See application file for complete search history.

(56) References Cited

U.S. PATENT DOCUMENTS

| | | | |
|---|---|---|---|
| 5,970,980 A | 10/1999 | Adair | |
| 6,091,058 A | 7/2000 | Faries, Jr. et al. | |
| 6,132,368 A | 10/2000 | Cooper | |
| 6,375,006 B1 | 4/2002 | Samuels | |
| 6,586,354 B1 | 7/2003 | Topolkaraev et al. | |
| 6,671,581 B2 | 12/2003 | Niemeyer et al. | |
| 6,824,511 B1 | 11/2004 | Bell et al. | |
| 7,666,191 B2 | 2/2010 | Orban, III et al. | |
| 7,727,244 B2* | 6/2010 | Orban, III | A61B 46/10 600/102 |
| 7,886,743 B2* | 2/2011 | Cooper | A61B 46/10 606/130 |
| 8,202,278 B2 | 6/2012 | Orban, III et al. | |
| 8,220,468 B2 | 7/2012 | Cooper et al. | |
| 8,273,076 B2 | 9/2012 | Devengenzo et al. | |
| 8,545,515 B2 | 10/2013 | Prisco et al. | |
| 8,592,582 B2 | 11/2013 | Fukunishi et al. | |
| 9,060,678 B2 | 6/2015 | Larkin et al. | |
| 10,932,877 B2* | 3/2021 | Devengenzo | A61B 46/10 |
| 11,039,820 B2* | 6/2021 | Beira | A61B 34/30 |
| 2006/0235436 A1* | 10/2006 | Anderson | A61B 34/71 606/1 |
| 2007/0129634 A1 | 6/2007 | Hickey et al. | |
| 2007/0239172 A1 | 10/2007 | Lee et al. | |
| 2008/0001559 A1 | 1/2008 | Schena | |
| 2010/0222725 A1 | 9/2010 | Munzel et al. | |
| 2010/0292707 A1 | 11/2010 | Ortmaier et al. | |
| 2011/0277775 A1 | 11/2011 | Holop et al. | |
| 2011/0277776 A1 | 11/2011 | McGrogan et al. | |
| 2012/0083768 A1 | 4/2012 | Skora et al. | |
| 2012/0232566 A1 | 9/2012 | Orban, III et al. | |
| 2012/0247489 A1 | 10/2012 | Orban, III et al. | |
| 2013/0199544 A1 | 8/2013 | Fortier et al. | |
| 2013/0289586 A1 | 10/2013 | Mazzucco et al. | |
| 2013/0325031 A1 | 12/2013 | Schena et al. | |
| 2013/0325033 A1 | 12/2013 | Schena et al. | |
| 2014/0338676 A1 | 11/2014 | Marinchak | |
| 2015/0000676 A1 | 1/2015 | Colona | |
| 2015/0202009 A1 | 7/2015 | Nussbaumer et al. | |
| 2016/0184037 A1 | 6/2016 | Cooper et al. | |
| 2017/0086934 A1 | 3/2017 | Devengenzo et al. | |
| 2019/0298469 A1 | 10/2019 | Ramstad et al. | |

FOREIGN PATENT DOCUMENTS

| | | | |
|---|---|---|---|
| CA | 2681965 A1 | 3/2003 | |
| CN | 1228688 A | 9/1999 | |
| CN | 101095638 A | 1/2008 | |
| CN | 101304702 A | 11/2008 | |
| CN | 101641044 A | 2/2010 | |
| CN | 201414848 Y | 3/2010 | |
| CN | 101801301 A | 8/2010 | |
| CN | 201823147 U | 5/2011 | |
| CN | 102208835 A | 10/2011 | |
| CN | 102596062 A | 7/2012 | |
| CN | 102946819 A | 2/2013 | |
| DE | 10122311 A1 | 12/2001 | |
| EP | 2559396 A2 | 2/2013 | |
| JP | H0586301 U | 11/1993 | |
| JP | 2000312685 A | 11/2000 | |
| JP | 2001187066 A | 7/2001 | |
| JP | 2001208978 A | 8/2001 | |
| JP | 2003033371 A | 2/2003 | |
| JP | 2003220077 A | 8/2003 | |
| JP | 2005237839 A | 9/2005 | |
| JP | 2006506128 A | 2/2006 | |
| WO | WO-9510986 A1 | 4/1995 | |
| WO | WO-2007041093 A1 | 4/2007 | |
| WO | WO-2007142698 A2 | 12/2007 | |
| WO | WO-2009123925 A1 | 10/2009 | |
| WO | WO-2015127231 A1 | 8/2015 | |
| WO | WO-2018013236 A1 | 1/2018 | |

OTHER PUBLICATIONS

Definition of "Cable" from https://www.thefreedictionary.com/support (Year: 2019).
Definition of "Support" from https://www.thefreedictionary.com/support (Year: 2019).
Extended European Search Report for Application No. EP15765258.7, dated Oct. 30, 2017, 9 pages.
International Search Report and Written Opinion for Application No. PCT/US15/20929, dated May 28, 2015, 18 pages.
International Search Report and Written Opinion for Application No. PCT/US2017/038350, dated Oct. 12, 2017, 14 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SURGICAL DRAPE AND SYSTEMS INCLUDING SURGICAL DRAPE AND ATTACHMENT SENSOR

CROSS-REFERENCE TO RELATED APPLICATIONS

This application is a continuation application of U.S. application Ser. No. 15/126,727, filed on Sep. 16, 2016, which is a U.S. national stage application under 35 U.S.C. § 371(c) of International Application No. PCT/US2015/020929, filed on Mar. 17, 2015, which claims the benefit of priority to U.S. Provisional Application No. 61/954,187, filed Mar. 17, 2014, each of which is incorporated by reference herein in their entirety.

TECHNICAL FIELD

Aspects of the present disclosure relate to surgical drapes for components of surgical systems and related devices and methods.

BACKGROUND

Remotely controlled surgical instruments, which can include teleoperated surgical instruments as well as manually operated (e.g., laparoscopic, thorascopic) surgical instruments, are often used in minimally invasive medical procedures. During surgical procedures, a patient side cart of a teleoperated surgical system is in close proximity to a patient. As a result, various portions of the patient side cart can come into contact with bodily fluids and other non-sterile substances and/or surfaces. Because motors, electronics, and/or other components of arms of the patient side cart may be damaged by a sterilization process, surgical drapes have been used to cover portions of an arm during a surgical procedure to minimize or eliminate the need to replace and/or perform a sterilization of the arm.

While surgical drapes have been effective, still further improvements upon surgical drapes are desirable. For example, it may be desirable to facilitate drape installation and management in preparation for surgical procedures.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical drape for a patient side cart of a teleoperated surgical system may comprise a body and an attachment device feature. The body may be sized and shaped to cover at least a portion of an arm or main column of the patient side cart. The attachment device feature may be connected to body. The attachment device feature may be configured to install the surgical drape to the arm or main column so as to cover at least a portion of the arm or main column with the surgical drape. The attachment device feature may be detectable by a sensor in an installed position of the surgical drape on the arm or main column.

In accordance with another exemplary embodiment, a patient side cart for a teleoperated surgical system may comprise a base, a main column connected to the base, and an arm connected to the main column to support a surgical instrument. At least one of the main column and the arm may include a sensor that, in an installed position of a surgical drape on the arm or main column, detects a presence of an attachment device feature of the surgical drape.

In accordance with another exemplary embodiment, a surgical drape for a patient side cart of a teleoperated surgical system may comprise a body and an attachment device feature. The body may be sized and shaped to cover at least a portion of a main column of the patient side cart. The attachment device feature may be configured to install the surgical drape to the main column.

In accordance with another exemplary embodiment, a method of installing a surgical drape for a patient side cart of a surgical system may comprise detecting a presence or absence of an attachment device feature of the surgical drape. Wherein, if the presence of the attachment device feature is detected, the surgical drape is in an installed state on a portion of the patient side cart. The method may further comprise transmitting feedback regarding an installation status of the surgical drape on the portion of the patient side cart based on the detecting.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
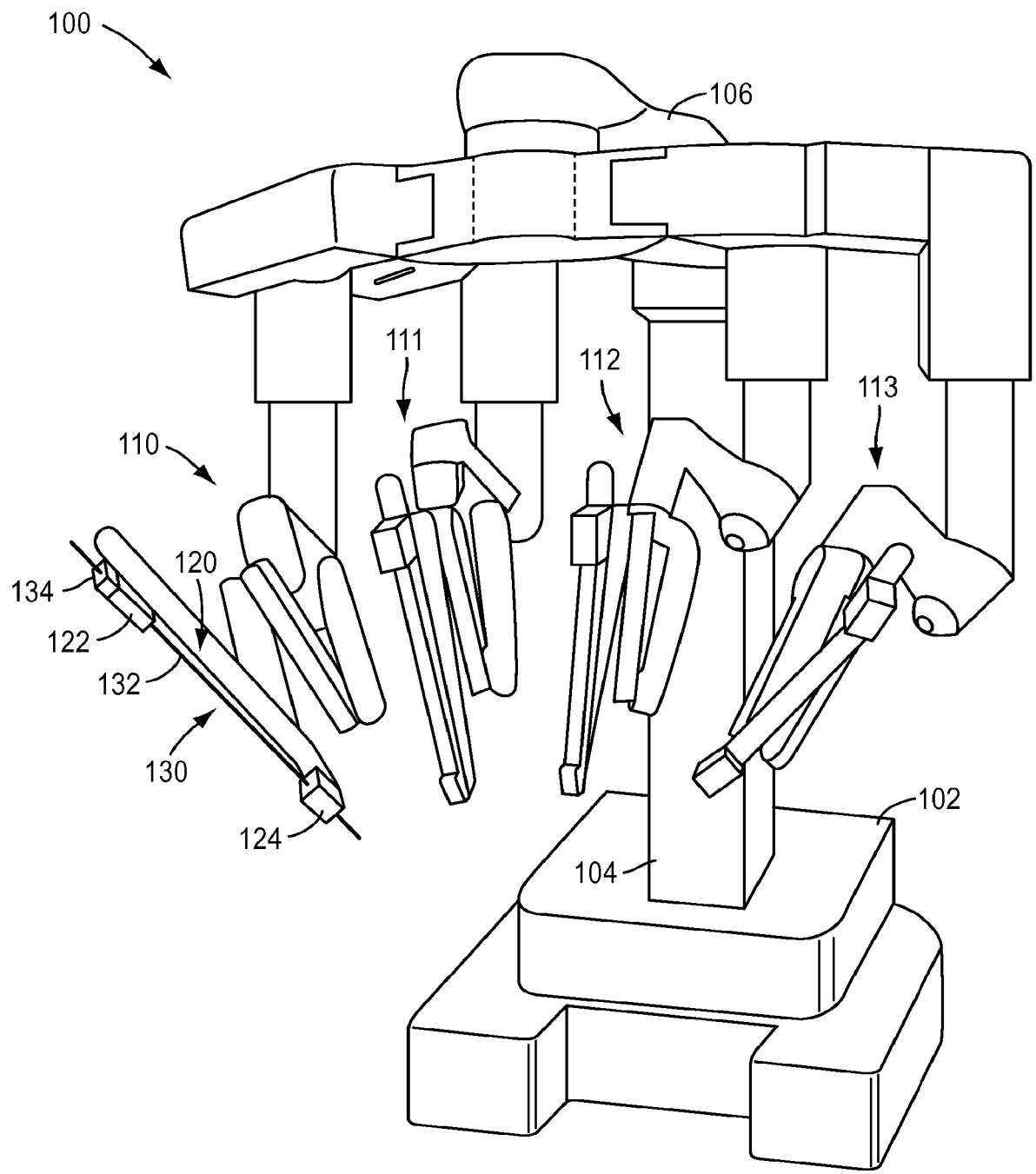
FIG. 1 is a perspective view of a patient side cart, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

The present disclosure contemplates various surgical drapes for covering portions of a patient side cart of a teleoperated surgical system that include features to facilitate installation of the surgical drape. For example, features may be provided to assist with handling of the drape, such as to facilitate how the drape is held and to facilitate maintenance of sterile field. In another example, a system may sense whether a drape is installed and provide feedback to a user regarding the installation status of a drape. Further, a material of a drape may be selected, for example, based upon the particular intended use of the drape.

Various exemplary embodiments of the present disclosure contemplate surgical drapes to cover at least a portion of an arm or at least a portion of a main column of a patient side cart of a teleoperated surgical system. Surgical drapes in accordance with various exemplary embodiments may be made of, for example, thermoplastic polyurethane, ultra-high molecular weight polyethylene, low density polyethylene, or high density polyethylene, nylon, polytetrafluoroethylene, polypropylene, polyethylene terephthalate (PET), or polyester, such as when used to cover a portion of an arm of a patient side cart. In another example, the surgical drape may be made of, for example, low density polyethylene, such as when drape is used to cover at least a portion of the main column of a cart. The surgical drape may include an attachment device feature, such as, for example, a metal member, such as a ferrous metal member, or a magnet. The surgical drape may include a cable support joined to the drape, such as, for example a hook, so the cable support may be easily accessed by a user. The cable support may include an attachment device to attach the cable support to the object at least partially covered by the drape. The attachment device for the cable support may be separate and different from the attachment device feature for the drape or may be the same attachment device. Various features may assist with installation of drapes, such as, for example, a handling member that may include alignment apertures, a pocket for a user to insert hands inside, a sterile boundary indicator, a spar clip, and/or malleable strips to shape drapes, such as to shape a drape into a snug fit or to form a drape into a shape extending away from a covered object, such as, for example, into a channel shape or a compact folded pattern.

Various exemplary embodiments of the present disclosure further contemplate a patient side cart for a teleoperated surgical system, wherein the cart includes an attachment mechanism to engage with and secure a drape. The cart may include, for example, a base, a main column connected to the base, and at least one arm connected to the main column to support a surgical instrument. At least one of the main column and the arm may include an attachment device feature to connect a surgical drape. The attachment device may be a metal member, such as, for example, a ferrous metal member, or a magnet. The magnet may have a shape of, for example, a ring, circle, square, rectangle, or other shape. At least one of the main column and the arm may further include a sensor to detect that a surgical drape has been installed. The sensor may be, for example, an inductive sensor, such as when the attachment device includes a metal member and a magnet. According to an exemplary embodiment, each of the arm and the main column can include an attachment device feature and a sensor.

Referring now to FIG. 1, an exemplary embodiment of a patient side cart 100 of a teleoperated surgical system is shown. A teleoperated surgical system may further include a surgeon console (not shown) for receiving input from a user to control instruments of patient side cart 100, as well as an auxiliary control/vision cart (not shown), as described in for example, U.S. Pub. No. US 2013/0325033, entitled "Multi-Port Surgical Robotic System Architecture" and published on Dec. 5, 2013, and U.S. Pub. No. US 2013/0325031, entitled "Redundant Axis and Degree of Freedom for Hardware-Constrained Remote Center Robotic Manipulator" and published on Dec. 5, 2013, each of which is hereby incorporated by reference in its entirety. By way of non-limiting example, a teleoperated surgical system of the type contemplated by the present disclosure includes a da Vinci® Surgical System available from Intuitive Surgical, Inc.

Patient side cart 100 may include a base 102, a main column 104, and a main boom 106 connected to main column 104. Patient side cart 100 also may include a plurality of arms 110, 111, 112, 113, which may each be connected to main boom 106. Portions of arms 110, 111, 112, 113 may include an instrument mount portion 120 to which an instrument 130 may be mounted, as illustrated for arm 110. Arms 110, 111, 112, 113 may be manipulated during a surgical procedure according to commands provided by a user at the surgeon console. In an exemplary embodiment, signal(s) or input(s) transmitted from a surgeon console may be transmitted to the control/vision cart, which may interpret the input(s) and generate command(s) or output(s) to be transmitted to the patient side cart 100 to cause manipulation of an instrument 130 (only one such instrument being mounted in FIG. 1) and/or portions of arm 110 to which the instrument 130 is coupled at the patient side cart 100.

Instrument mount portion 120 may comprise an actuation interface assembly 122 and an accessory mount 124, with a shaft 132 of instrument 130 extending through accessory mount 124 (and on to a surgery site during a surgical procedure) and a force transmission mechanism 134 of instrument connecting with the actuation interface assembly 122, according to an exemplary embodiment. Accessory mount 124 may be configured to hold a cannula (not shown) through which shaft 132 of instrument 130 may extend to a surgery site during a surgical procedure. Actuation interface assembly 122 may contain a variety of mechanisms that are controlled to respond to input commands at the surgeon console and transmit forces to the force transmission mechanism 134 to actuate instrument 130.

Although the exemplary embodiment of FIG. 1 shows an instrument 130 attached to only arm 110 for ease of viewing, an instrument may be attached to any and each of arms 110, 111, 112, 113. An instrument 130 may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site. In the exemplary of FIG. 1, either a surgical instrument with an end effector or a camera instrument may be attached to and used with any of arms 110, 111, 112, 113. However, the embodiments described herein are not limited to the exemplary embodiment of FIG. 1 and various other teleoperated surgical system configurations may be used with the exemplary embodiments described herein.

During a surgical procedure that uses one or more instrument(s) attached to arm(s) of a patient side cart, the arm(s) are in close proximity to a surgical site. As a result, the arm(s) of the surgical system could become contaminated. Replacement of an arm involves cost and although sterilization could be undertaken, sterilization procedures (e.g., autoclaving) risks damaging components of the arm that are sensitive to heat, such as, for example, motors, electronics, and other arm components. In view of these considerations, at least a portion of an arm of patient side cart may be covered by a surgical drape during a surgical procedure to minimize or eliminate contamination of the arm.

Figure 2:
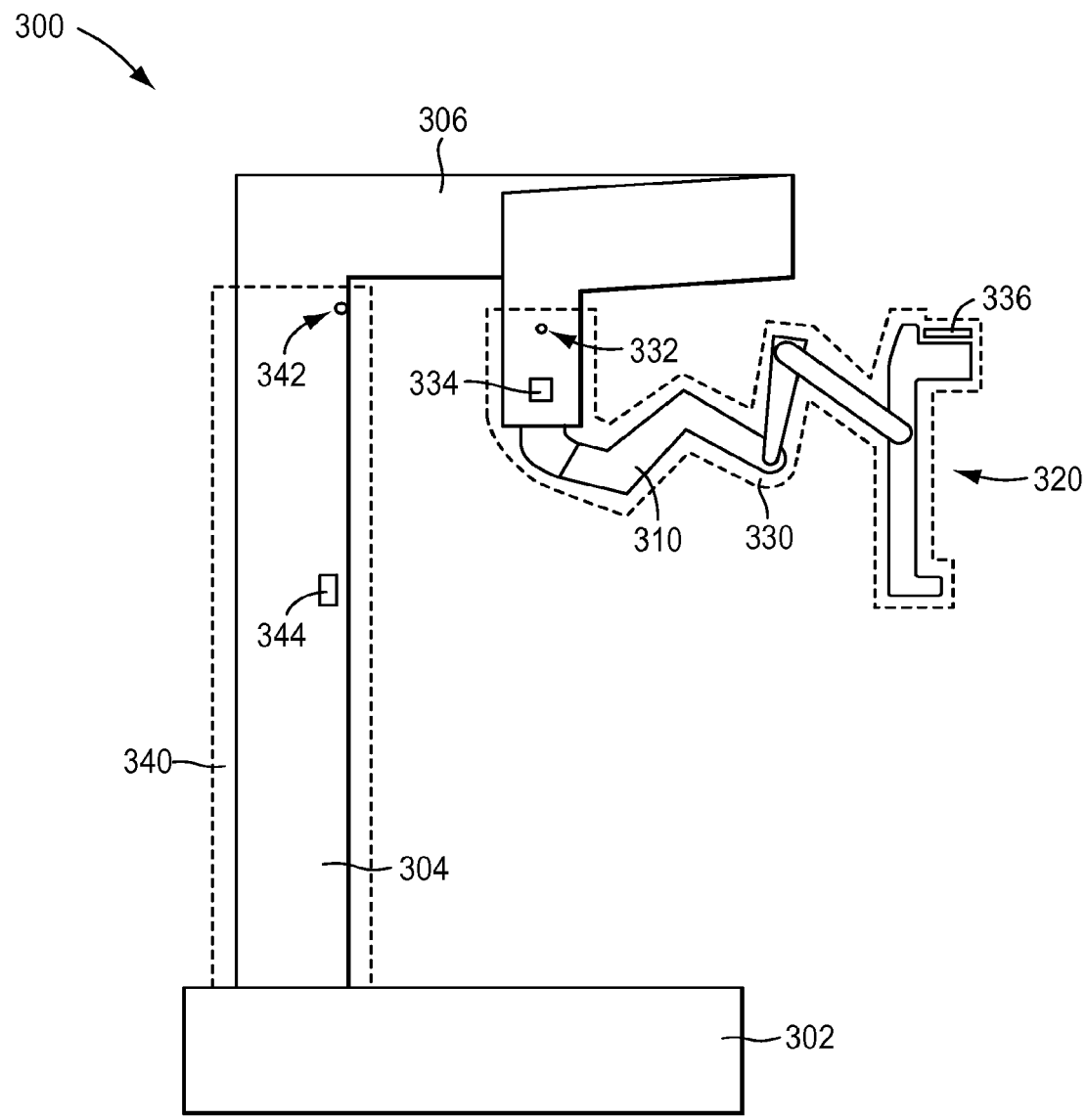
FIG. 2 is a side view of a patient side cart with surgical drapes shown schematically, according to an exemplary embodiment.

Turning to FIG. 2, a side view is shown of a patient side cart 300 of a teleoperated surgical system. Patient side cart 300 may be configured according to the exemplary embodiment of FIG. 1 and may include a base 302, a main column 304, and a main boom 306 to which a plurality of arms, such as arm 310 may be connected, according to an exemplary embodiment. Arm 310 may include an instrument mount portion 320, as discussed above with regard to the exemplary embodiment of FIG. 1. In the exemplary embodiment of FIG. 2, a surgical drape 330 for arm 310 is schematically shown with dashed lines to illustrate how surgical drape 330 may cover at least a portion of arm 310 to minimize or eliminate contamination of arm 310. Surgical drape 330 may include an attachment device 332 to attach surgical drape 330 to arm 310, as will be discussed in detail below. Although a single attachment device 332 is shown in the exemplary embodiment of FIG. 2, the exemplary embodiments described herein are not limited a single attachment device 332 and may instead include, for example, two, three, four, or any number of attachment devices 332.

According to an exemplary embodiment, surgical drape 330 also can include a cable support 334, such as, for example, a hook. Cable support 334 may be used to support a cable extending from a component of an arm or instrument, such as, for example, a data signal cable and/or fiber optic cable extending from an instrument (not shown) (e.g., including an imaging instrument) attached to an arm of patient side cart 300. Although a single cable support 334 is shown in the exemplary embodiment of FIG. 2, the exemplary embodiments described herein are not limited a single cable support 334 and may instead include, for example, two, three, four, or more cable supports 334. Further, surgical drape 330 may be provided without a cable support 334. Although the various exemplary embodiments of drapes described herein may include a cable support, the drape may lack a cable support, which may instead be connected to a patient side cart. For example, cable support 334 may instead be connected to arm 310.

A sterile adaptor 336 may be attached to surgical drape 300 to provide an interface between an instrument (not shown), which is located on a sterile side of surgical drape 300, and arm 310, which is located on a non-sterile side of surgical drape 300, according to an exemplary embodiment. The instrument may be attached to instrument mount portion 320 of arm 310 via sterile adaptor 336. Sterile adaptor 336 may be provided to maintain a barrier between the sterile side of surgical drape 300 and the non-sterile side of surgical drape 300, while permitting the transmission of mechanical and electrical energy and signals between the instrument and the arm 310. For example, sterile adaptor 336 may serve as an interface between the actuation interface assembly 122 and the force transmission mechanism 134 of the exemplary embodiment of FIG. 1 so that mechanical and electrical energy and signals may be transferred between the actuation interface assembly 122 and the force transmission mechanism 134. Various exemplary embodiments of sterile adaptors are disclosed, for example, in U.S. Pat. No. 7,666,191 (entitled "Robotic Surgical System with Sterile Surgical Adaptor"), issued Feb. 23, 2010, which is hereby incorporated by reference in its entirety.

Although surgical drapes may be used on arms of a patient side cart because the arms are in close proximity to a surgical site, surgical drapes also may be used on other portions of a patient side cart that could otherwise be contaminated during a surgical procedure. For instance, main column 304 of patient side cart 300 may be close enough to a surgical site to have the potential to come into contact with various substances (e.g., body fluids, etc.) and/or other non-sterile surfaces. Therefore, at least a portion of main column 304 may be covered with a surgical drape 340, which is schematically shown in the exemplary embodiment of FIG. 2 with dashed lines. Surgical drape 340 may include an attachment device 342 to attach surgical drape 340 to main column 304. Although a single attachment device 342 is shown in the exemplary embodiment of FIG. 2, the exemplary embodiments described herein are not limited a single attachment device 342 and may instead include, for example, two, three, four, or any number of attachment devices 342. As with surgical drape 330, surgical drape 340 also may include one or more cable supports 344 to support a cable extending from a component of an arm or instrument, although surgical drape 340 may be provided without one or more cable supports 344. According to an exemplary embodiment, surgical drape 340 may cover the entirety of main column 304 between main boom 306 and base 302, as shown in FIG. 2, or surgical drape may cover a portion of main column 304 between main boom 306 and base 302.

Figure 3:
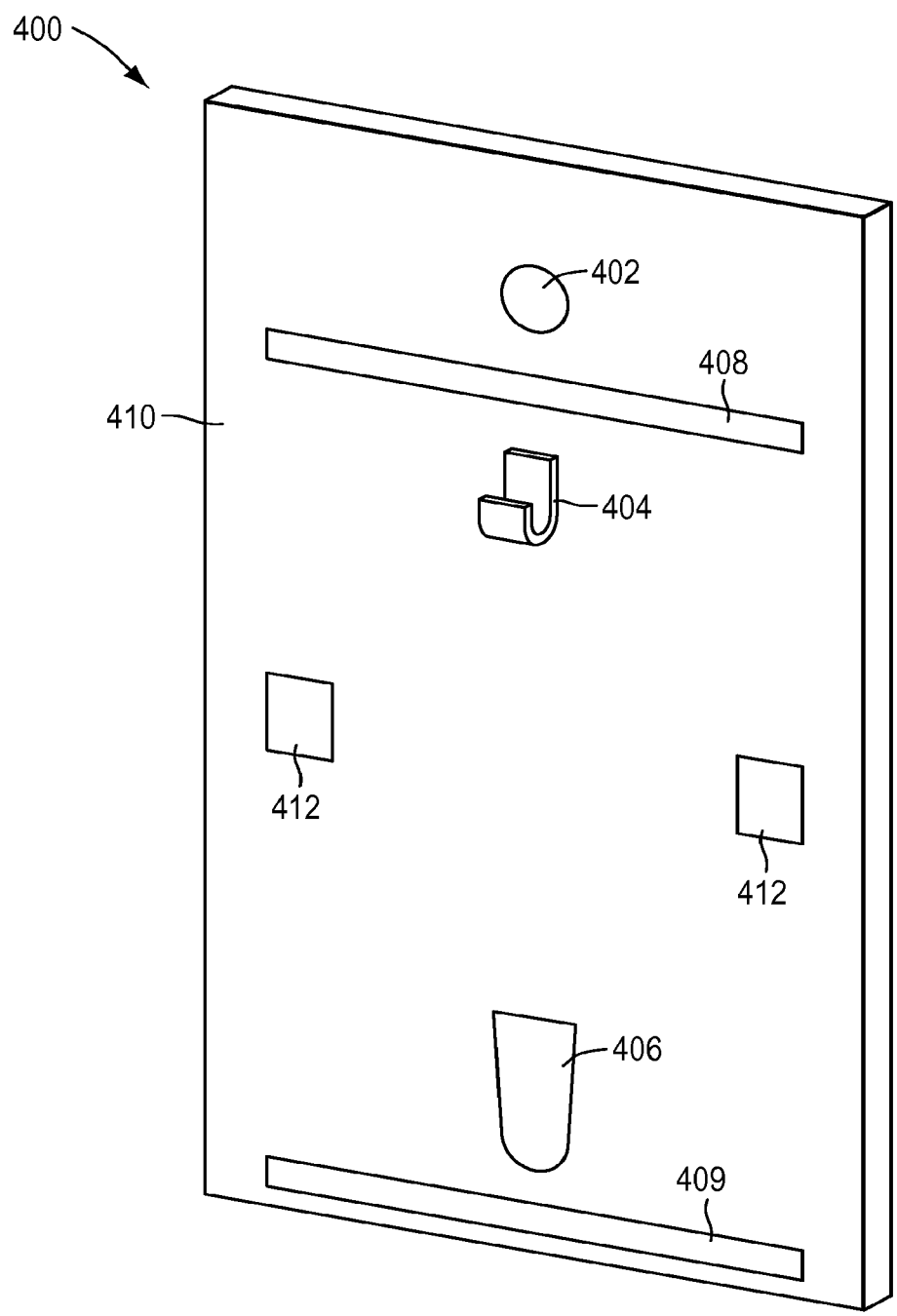
FIG. 3 is a perspective view of a surgical drape, according to an exemplary embodiment.

Turning to FIG. 3, an exemplary embodiment of a surgical drape 400 is shown. Surgical drape 400 may be a surgical drape 330 for covering at least a portion of an arm 310 or a surgical drape 340 for covering at least a portion of main column 304, according to the exemplary embodiment of FIG. 2. Surgical drape 400 may comprise a body 410 that covers at least a portion of an arm 310 or at least a portion of main column 304 of a patient side cart. Body 410 may be, for example, in the form of a sheet, tube, or other form familiar to one of ordinary skill in the art. Body 410 is depicted as having a generally flat, rectangular shape in the exemplary embodiment of FIG. 3 for ease of viewing, but the exemplary embodiments described herein are not limited to a flat, rectangular body 410 and may have other shapes and/or than those depicted in the exemplary embodiment of FIG. 3. For example, a body of a surgical drape may have a shape corresponding to the portion of an arm or main column it is designed to cover.

Body 410 may be made of a polymer material suitable for a surgical drape. According to an exemplary embodiment, body 410 may comprise, for example, polyethylene, polyurethane, polycarbonate, ultra-high molecular weight polyethylene, low density polyethylene, high density polyethylene, nylon, polytetrafluoroethylene, polypropylene, PET, polyester, or combinations thereof. According to an exemplary embodiment, body 410 may be made of the same material when surgical drape 400 is a surgical drape 330 for covering at least a portion of an arm 310 or a surgical drape 340 for covering at least a portion of main column 304, according to the exemplary embodiment of FIG. 2.

According to another exemplary embodiment, body 410 may be made of differing materials based on whether drape 400 is used as a surgical drape 330 for covering at least a portion of an arm 310 or a surgical drape 340 for covering at least a portion of main column 304. If drape 400 is used as a surgical drape 330 for covering at least a portion of an arm 310, a material may be selected in view of properties that may be desirable for a drape 330 used for such installation. For example, a drape material may be selected that is flexible because a portion of arm 310 may be actuated during a surgical procedure, abrasion resistant because drape 330 may rub against itself when arm 310 is actuated or may contact other objects (such as when arm 310 collides with another arm), has a smooth surface to minimize abrasion between surfaces of the drape, and/or various other properties, such as, for example, transparency (or translucence), ease of folding, and low linting.

According to an exemplary embodiment, when drape 400 is used as a surgical drape 330 for covering at least a portion of an arm 310, body 410 may be made of, for example, thermoplastic polyurethane (TPU), ultra-high molecular weight polyethylene, low density polyethylene (LDPE), high density polyethylene (HDPE), CSR wrap material (central supply room material, which is typically a natural cellulose fiber), nylon blends, polypropylene, polyester, and other materials familiar to one of ordinary skill in the art. The material of body 410 may further include fillers to affect the properties of the material used for body 410. For example, the material of body 410 may include fillers to affect, for example, the color, texture, and/or anti-static properties of body 410.

In another example, the material of body 410 may include a lubricant filler to reduce the tackiness of the material and minimize the material sticking to or abrading against itself, which may also facilitate handling of the drape during installation. According to an exemplary embodiment, the material of body 410 may have a coefficient of friction ranging from, for example, about 0.10 to about 0.15. According to an exemplary embodiment, TPU may include a lubricant filler and have a coefficient of friction ranging from, for example, about 0.11 to about 0.13. An example of TPU including a lubricant filler is the material of part number IS-2001 from American Polyfilm. A body 410 made of the various materials discussed above may include a coating, such as, for example, a polytetrafluoroethylene (PTFE) coating, such as a Teflon® from DuPont. Further, when drape 400 is used as a surgical drape 330 for covering at least a portion of an arm 310, body 410 may have a thickness ranging, for example, from about 0.001 inches to about 0.008 inches.

According to an exemplary embodiment, when drape 400 is used as a surgical drape 340 for covering at least a portion of main column 304, body 410 may be made of a material with properties suitable for use on main column 304. According to an exemplary embodiment, body 410 may be made of, for example, TPU, ultra-high molecular weight polyethylene, LDPE, HDPE, CSR wrap material (central supply room material, which is typically a natural cellulose fiber), nylon blends, polypropylene, polyester, and other materials familiar to one of ordinary skill in the art. When used for drape 340, body 410 may be made of a material that minimizes cling to itself and resistance puncture, according to an exemplary embodiment. Body 410 may be made of, for example, LDPE, and other materials familiar to one of ordinary skill in the art. According to an exemplary embodiment the material of body 410 may include one or more fillers to affect the properties of the material of body 410. For example, a material of body 410 may include an antistatic filler to reduce electrostatic charge that may cause the drape to cling to itself or other objects, thus facilitating handling of the drape. The antistatic filler may be, for example, P/N Further, the thickness of drape 400 on main column 304 may be less than thickness of drape 330 for arm 310. Body 410 may have a thickness ranging, for example, from about 0.0010 inches to about 0.0015 inches when used in drape 340.

Although body 410 may be depicted as a single piece in the exemplary embodiment of FIG. 3, body 410 may comprise a plurality of pieces of the various materials discussed above that have been joined together. Multiple body pieces may be joined, for example, via adhesive bonding, thermal welding, radio frequency welding, and other techniques familiar to one of ordinary skill in the art. According to an exemplary embodiment, when drape 400 is used as a surgical drape 330 for covering at least a portion of an arm 310, body 410 may be a single layer of material (e.g., any of the materials described herein, or combinations thereof), although multiple layers also may be used.

According to an exemplary embodiment, when drape 400 is used as a surgical drape 340 for covering at least a portion of main column 304, body 410 may include multiple layers, although a single layer also could be used. For example, body 410 for surgical drape 340 may include three layers, with the outside (first and third) layers being made of a material that minimizes clinging of the material to itself, such as, for example, LDPE with an antistatic filler, and the middle (second) layer being made of a puncture resistance material, such as, for example, pure LDPE. However, body 410 for drape 400 when used as surgical drape 340 is not limited to three layers and instead may include, for example, one, two, three, four, or more layers.

Surgical drape 400 may include one or more attachment devices to attach surgical drape 400 to the portion of a patient side cart the drape 400 is covering. According to an exemplary embodiment, surgical drape 400 may include a first part 402 of an attachment device. The portion of the patient side cart to which surgical drape 400 is attached may have a corresponding second part of the attachment device to which the first part 402 is joined to attach the drape. Although only one first part 402 of an attachment device is shown in the exemplary embodiment of FIG. 3, the exemplary embodiments described herein are not limited to a single attachment device and may instead include two, three, four, or more such attachment devices.

As will be discussed in detail below, a sensor of the patient side cart may be configured to detect when surgical drape 400 has been attached to a patient side cart, such as, for example, an arm 310 or main column 304 of a patient side cart 300. According to an exemplary embodiment, a sensor of a patient side cart may detect when a surgical drape 400 has been attached by detecting the presence of first part 402 of an attachment device (e.g., first part 402 interacts with the sensor). The sensor of the patient side cart may be configured to transmit a signal to a controller in the patient side cart once attachment of surgical drape 400 has been detected. Otherwise, if the controller has not received a signal from the sensor, the surgical system may be configured to issue feedback to a user or other personnel associated with preparing the surgical system for use. Such feedback can include, but is not limited to, for example, an audible and/or visual warning at a surgeon's console and/or an auxiliary unit of the surgical system, according to an exemplary embodiment. Thus, attachment device 402 and the sensor of the patient side cart may serve as a reminder to install a drape on one or more portions of a patient side cart.

Surgical drape 400 may include other features besides an attachment device 402. According to an exemplary embodiment, surgical drape 400 may include one or more attachment devices 412 configured to attach surgical drape 400 to a portion of a patient side cart without interacting with a sensor to detect attachment of the drape. Attachment devices 412 may be chosen from, for example, a variety of mechanical fasteners (e.g., snap fasteners), magnetic fasteners, or other types of fasteners familiar to one of ordinary skill in the art. Surgical drape 400 may further include one or more cable supports, such as a hook 404, as discussed above with regard to the exemplary embodiment of FIG. 2. According to an exemplary embodiment, hook 404 may be attached to drape 400 itself by joining hook 404 to body 410 via, for example, adhesive bonding, heat sealing, or other techniques familiar to one of ordinary skill in the art. By attaching hook 404 to surgical drape 400 instead of to an arm or main column underneath drape 400, hook 404 may be easily accessed by a user to support a cable from a component or instrument, such as a data signal or electrical cable from a surgical or imaging instrument mounted at the patient side cart. According to an exemplary embodiment, hook 404 may be present on a drape for an arm, such as drape 330 for arm 310 of the exemplary embodiment of FIG. 2, but may be absent for a drape of a main column, such as drape 340 for main column 304 of the exemplary embodiment of FIG. 2.

Surgical drape 400 may include other structures in combination with or independently of any of those described above, according to an exemplary embodiment. For example, surgical drape 400 may include one or more shaping devices 408 to bend and shape surgical drape 400 about a component drape 400 is intended to cover. A shaping device 408 may be, for example, a malleable strip (e.g., a malleable metal strip or wire) configured to substantially retain a shape the strip is bent into. Shaping device 408 may be used to shape surgical drape 400 into a desired shape, such as, for example, to make surgical drape 400 fit more snugly about a portion of a patient side cart surgical drape 400 is attached to by deforming the malleable strip about the portion of the patient side cart so drape 400 has a shape corresponding to the covered portion of the patient side cart. Shaping devices may also be used as weights to help keep surgical drape 400 in place. For example, surgical drape 400 may include a shaping device 409 at the bottom of surgical drape 400 that acts as a weight to hold surgical drape 400 in place.

Surgical drape 400 may include a sterile adaptor 406, such as sterile adaptor 336 of the exemplary embodiment of FIG. 2, such as when surgical drape 400 is for covering at least a portion of an arm of a patient side cart, although surgical drape 400 need not include sterile adaptor 406 when surgical drape 400 is configured to cover at least a portion of a main column of a patient side cart, according to an exemplary embodiment.

Figure 4:
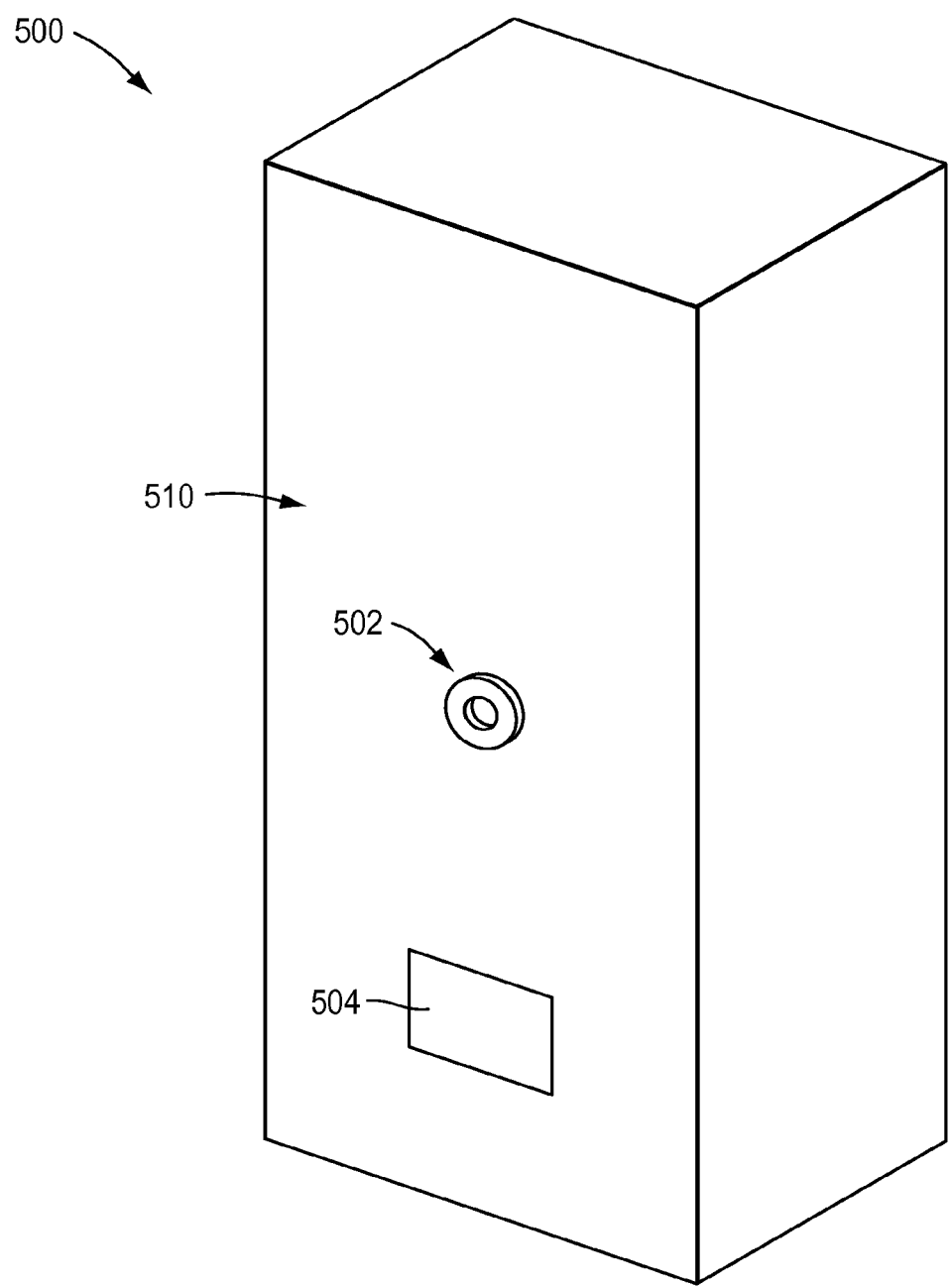
FIG. 4 is a perspective view of a portion of a patient side cart, according to an exemplary embodiment.

As discussed above with regard to the exemplary embodiment of FIG. 3, an attachment device of a surgical drape may include separate parts, such as first and second parts, configured to engage with one another when joined together so the drape may be attached to the cart. Turning to FIG. 4, a perspective view is shown of a portion 500 of a patient side cart to which a surgical drape is to be attached, such as, for example, surgical drape 400 of the exemplary embodiment of FIG. 3. Patient side cart portion 500 may be, for example, a part of an arm, such as arm 310 of the exemplary embodiment of FIG. 2, or a part of a main column, such as main column 304 of the exemplary embodiment of FIG. 2.

As shown in the exemplary embodiment of FIG. 4, patient side cart portion 500 may include a second part 502 of an attachment device, such as on a surface 510 of patient side cart portion 500. Second part 502 of the attachment device may be configured to engage with a first part of the attachment device on a surgical drape to attach the drape to patient side cart portion 500, such as by engaging with first part 402 of the attachment device of the exemplary embodiment of FIG. 3. According to an exemplary embodiment, attachment device may be a magnetic attachment device. For example, one of first part 402 and second part 502 may be a magnet and the other may be a metal member, such as a ferrous metal member that would be attracted by the magnet. According to an exemplary embodiment, first part 402 of surgical drape 400 may be a metal member and second part 502 may be a magnet that the metal member is attracted to so surgical drape 400 is attached to patient side cart portion 500. According to an exemplary embodiment, first part 402 may be made of a neodymium iron boron alloy, or other magnetic alloy familiar to one of ordinary skill in the art, and second part may be made of a steel alloy or other metal alloy familiar to one of ordinary skill in the art.

Figure 6:
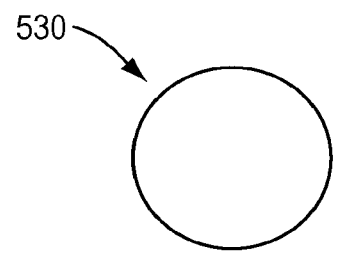
FIG. 6 is a top view of a magnetic attachment, according to another exemplary embodiment.
Figure 7:
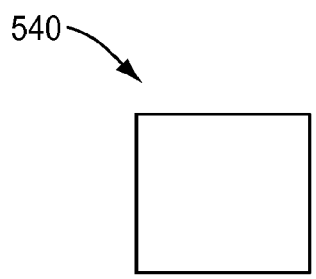
FIG. 7 is a top view of a magnetic attachment, according to yet another exemplary embodiment.
Figure 8:
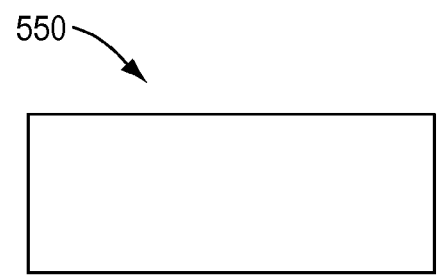
FIG. 8 is a top view of a magnetic attachment, according to another exemplary embodiment.
Figure 28:
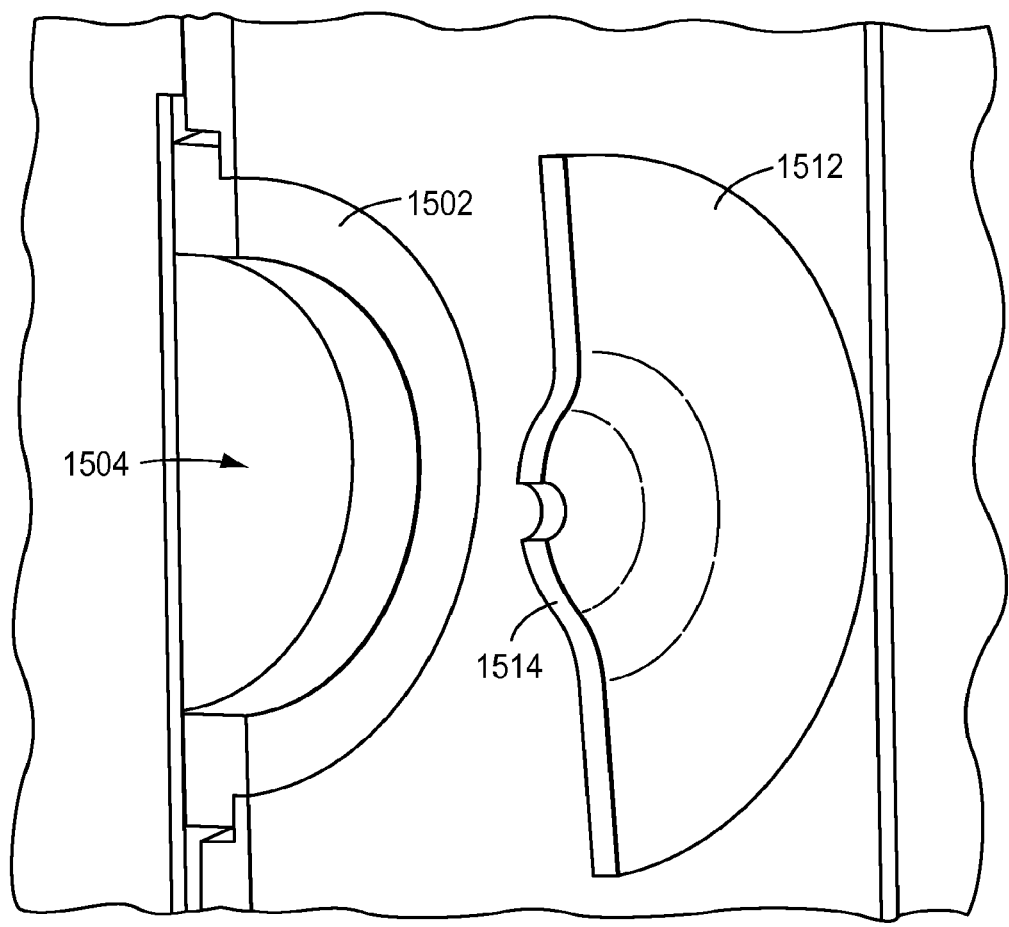
FIG. 28 is a sectional view of a magnet and a metal member, according to an exemplary embodiment.

The parts used for a magnetic attachment device may have various shapes. As shown in the exemplary embodiments of FIG. 5, a magnet 520 used in an attachment device, such as the second part 502 in the exemplary embodiment of FIG. 4, may have a ring shape. The corresponding metal member may have a circular shape. A circular shape, such as a ring shape, for the magnet may facilitate alignment of the attachment device parts, such as when the drape is attached to a portion of a patient side cart. For instance, precise alignment between corners of attachment parts is not needed when connecting attachment parts having circular shapes. The shapes of the magnet and metal member may facilitate engagement between the magnet and metal member. Turning to FIG. 28, a sectional view of a magnet 1502 and a metal member 1512 is shown. Magnet 1502 and metal member 1512 may be, for example, used as first part 402 and second part 502 in the exemplary embodiments of FIGS. 3 and 4. Metal member 1512 may include a protrusion 1514 to facilitate engagement of metal member 1512 with magnet 1502. For instance, protrusion 1514 may center metal member 1512 upon magnet 1502. When magnet 1502 has a ring shape with a central aperture 1504, protrusion 1514 may be received within central aperture 1504. Protrusion 1514 may also minimize or prevent lateral sliding of metal member 1512 relative to magnet 1502. Other shapes may be used for the magnet and metal member of the exemplary embodiments described herein, such as, for example, the circular shape 530 of the exemplary embodiment of FIG. 6, the square shape 540 of the exemplary embodiment of FIG. 7, the rectangular shape 550 of the exemplary embodiment of FIG. 8, and other various shapes.

Figure 9:
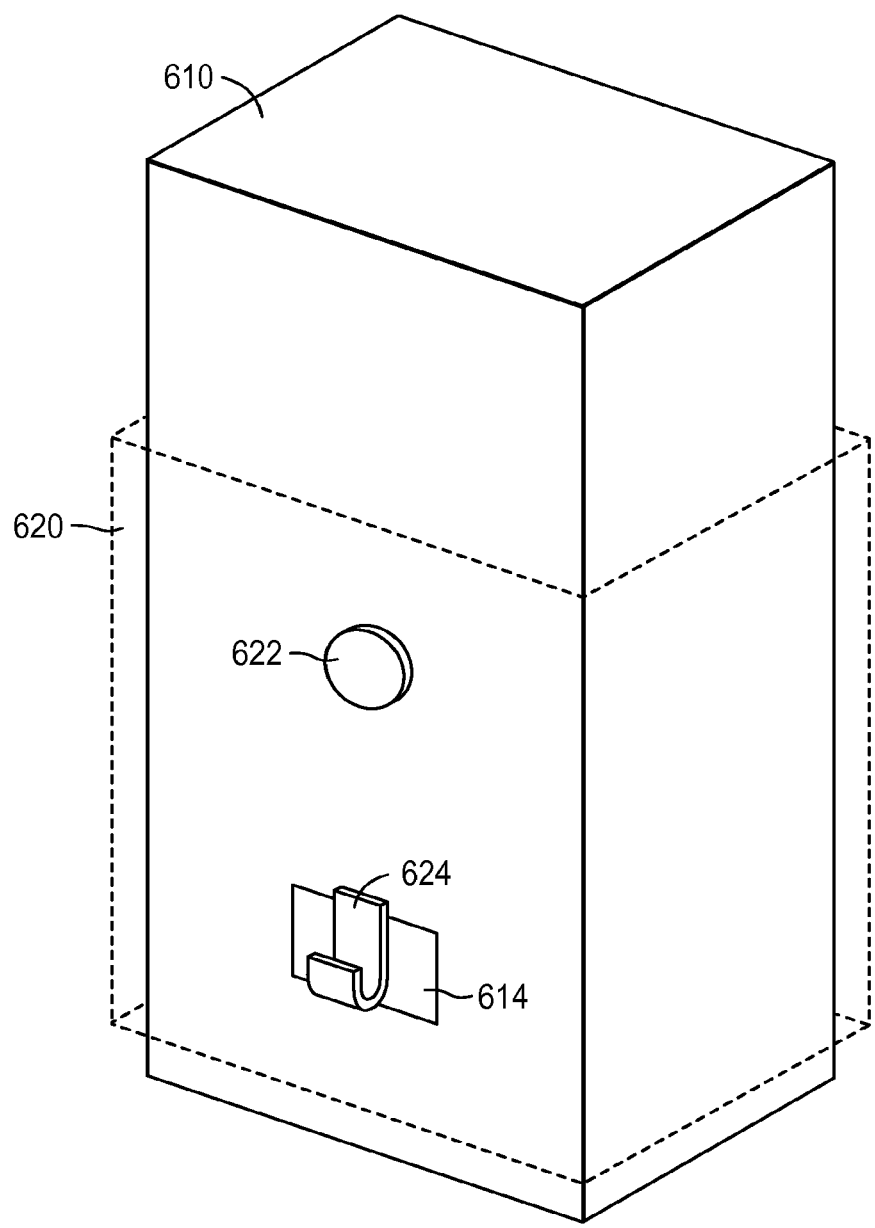
FIG. 9 is a perspective view of a portion of a patient side cart with a surgical drape shown schematically, according to an exemplary embodiment.

Turning to FIG. 9, a patient side cart portion 610 is shown in a state of being at least partially covered by a surgical drape 620, with surgical drape 620 being attached to patient side cart portion 610 via a drape attachment device. Patient side cart portion 610 may be, for example, an arm 310 or main column 304, as in the exemplary embodiment of FIG. 3, and surgical drape 620 may be a surgical drape 330 or 340, as in the exemplary embodiment of FIG. 3. The drape attachment device may include a first part 622, such as, for example, a metal member, and a second part, such as, for example, a magnet, which is covered by first part 622 in the view shown in the exemplary embodiment of FIG. 9. Surgical drape 620 further includes a cable support 624, such as, for example, a hook, which is shown in an attached state in the exemplary embodiment of FIG. 9 to patient side cart portion 610.

According to an exemplary embodiment, a cable support attachment device may be used to attach a cable support to a patient side cart. Although it may be desirable to attach a cable support to a patient side cart portion so the cable support is supported, it would be desirable to locate the cable support so it is not covered by a surgical drape and the cable support is easy to access. Therefore, according to an exemplary embodiment, a cable support attachment device may include a first part and a second part configured to engage with the first part to fix the cable support in place. As schematically shown in FIG. 4, a second part 504 of a cable support attachment device may be connected to a patient side cart portion 500 so a cable support may be fixed to, and supported by, patient side cart portion 500. In the exemplary embodiment of FIG. 9, cable support 624 is in an attached state to patient side cart portion 610 via a second part 614 of a cable support attachment device, with the first part of the cable support attachment device not visible in FIG. 9.

To make the cable support easily accessible, the first part of the cable support attachment device may be connected to or part of a cable support that is attached to a surgical drape. As a result, cable support 624 may be easily accessed because cable support 624 is fixed to a surface of surgical drape 620, instead of being located underneath surgical drape 620, as shown in the exemplary embodiment of FIG. 9. Further, even though cable support 624 is located on a sterile side of surgical drape 620, cable support 624 may be positively attached to, and supported by, patient side cart portion 610 via the cable support attachment device.

Figure 10:
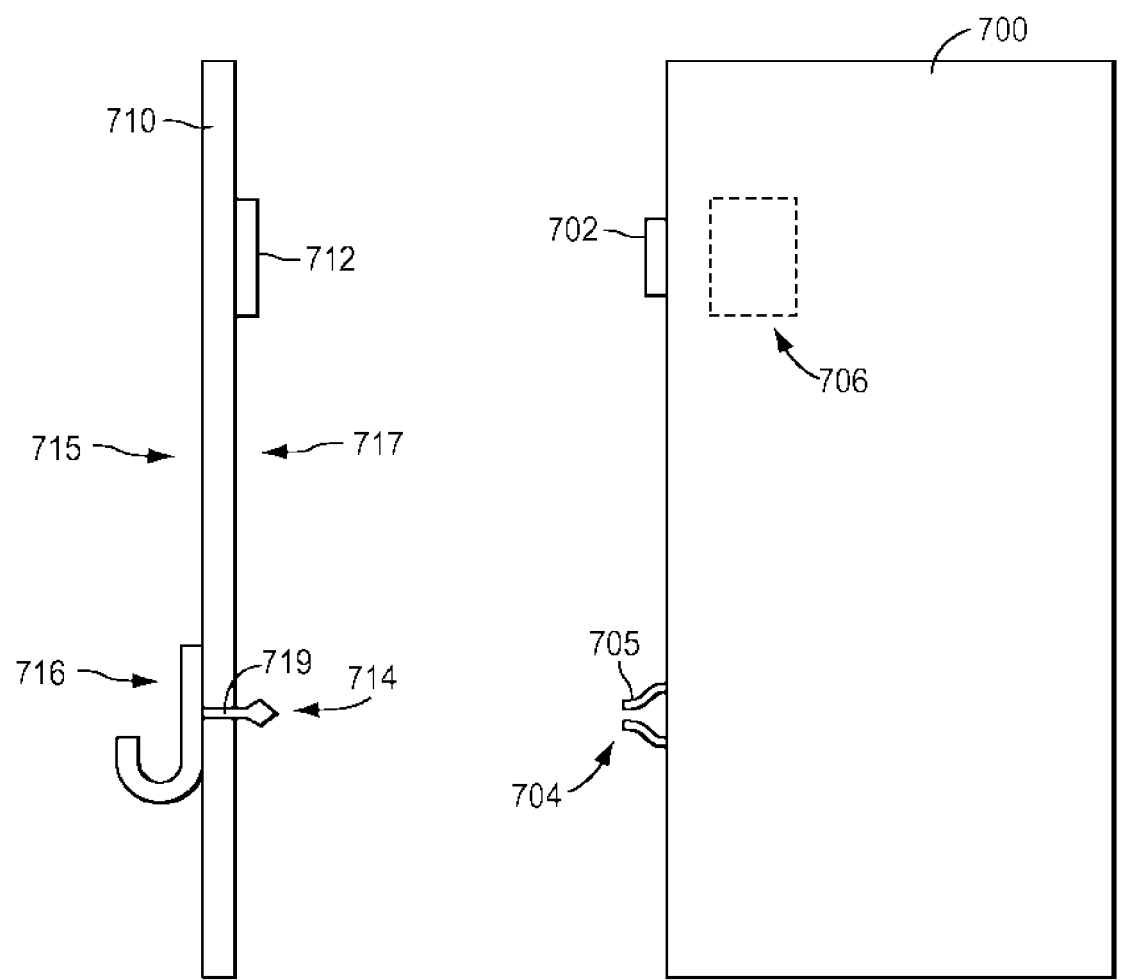
FIG. 10 is a side view of a surgical drape and a portion of a patient side cart in an unattached state, according to an exemplary embodiment.
Figure 11:
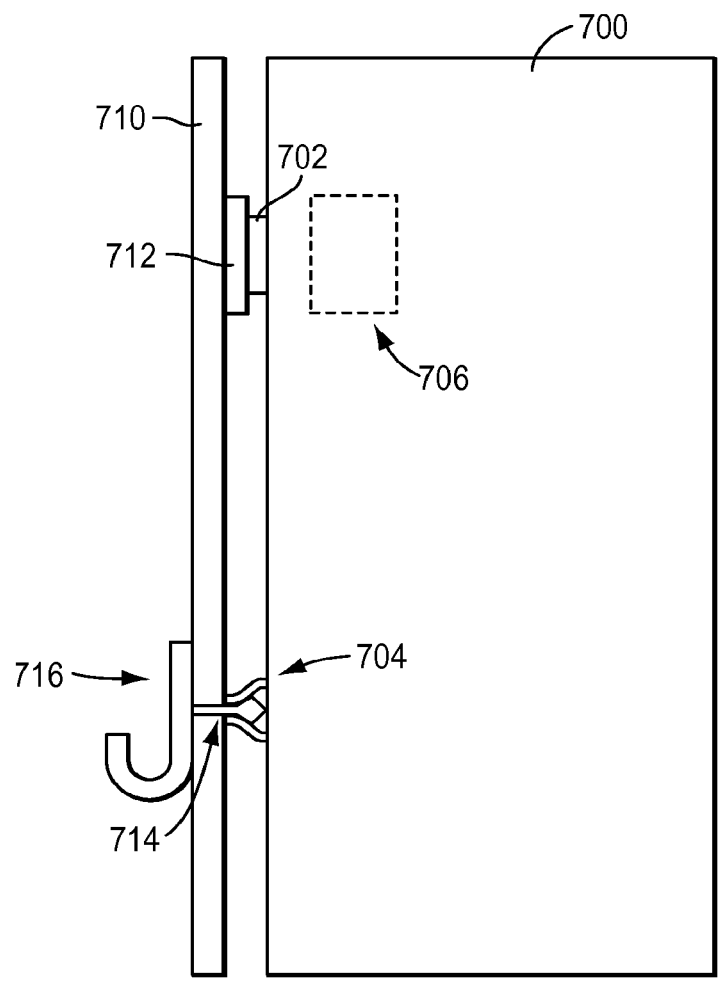
FIG. 11 shows the surgical drape and patient side cart portion of FIG. 10 in an attached state.

Turning to FIG. 10, a side view is shown of surgical drape 710 and a patient side cart portion 700 in an uninstalled state of drape 710, according to an exemplary embodiment. Patient side cart portion 700 may be, for example, an arm 310 or main column 304, as in the exemplary embodiment of FIG. 3, and surgical drape 710 may be a surgical drape 330 or 340, as in the exemplary embodiment of FIG. 3. Surgical drape 710 includes a first part 712 of a drape connection device configured to engage with a complementary second part 702 on portion 700 to attach surgical drape 710 to portion 700. Surgical drape 710 further includes a cable support 716 fixed to a sterile side 715 of surgical drape 710, which in turn may be attached to patient side cart portion 700 via a cable support connection device. According to an exemplary embodiment, cable support connection device may include a first part 714 connected to surgical drape 710 and extending from a non-sterile side 717 of surgical drape 710, with a second part 704 connected to patient side cart portion 700. First part 714 and second part 704 are configured to engage with one another so cable support 716 is connected to, and supported by, patient side cart portion 700, as shown in FIG. 11, which depicts surgical drape 710 and patient side cart portion 700 in an attached state.

A cable support attachment device may be a mechanical fastener, a magnetic attachment device, or other type of attachment device familiar to one of ordinary skill in the art. In the exemplary embodiment of FIGS. 10 and 11, the cable support attachment device is a latch, such as a spring latch or other latch familiar to one of ordinary skill in the art, although the cable support attachment devices of the exemplary embodiments described herein are not limited to a latch or a mechanical fastener. For example, first part 714 may be a male part with a projection 719 and second part 704 may be a female part, such as a spring-loaded latch 705 that projection 719 is inserted into, thereby attaching cable support 716 to patient side cart portion 700, as shown in the exemplary embodiments of FIGS. 10 and 11. Conversely, first part 714 may be a female part and second part 704 may be a male part inserted into first part 714.

As discussed in the exemplary embodiments above, a drape attachment device may be configured to interact with a sensor of a patient side cart. According to an exemplary embodiment, the sensor may be mounted to the patient side cart. The sensor may be used, for example, to detect that a surgical drape has been attached to a patient side cart. According to an exemplary embodiment, a first part of a drape attachment device may be configured to interact with a sensor of a patient side cart. Referring to FIGS. 10 and 11, when first part 712 of a drape attachment device attached to surgical drape 710 is engaged with second part 702 of the drape attachment device attached to patient side cart portion 700 to attach surgical drape 710 to patient side cart portion 700, a sensor 706 may detect the present of first part 712. Sensor 706 may subsequently transmit a signal indicating that surgical drape 710 has been attached, such as to the surgical system that includes the patient side cart. Thus, in the unattached state shown in FIG. 10, sensor 706 has not detected the presence of first part 712, and thus the drape; but in the attached state shown in FIG. 11, sensor 706 detects the presence of first part 712 of drape attachment device, indicating the installation of surgical drape 710.

A sensor configured to detect the presence of a drape attachment device, such as one part of a drape attachment device, may be, for example, an inductive sensor. An inductive sensor may emit a magnetic field that is sensed by the sensor, such as via an induction loop. Thus, when a metallic member is proximate the sensor, the metallic member changes the inductance, which is detected by the sensor to indicate the presence of the metallic member. According to an exemplary embodiment, first part 712 of drape attachment device may be a metal member and second part 702 may be a magnet, as discussed above with regard to the exemplary embodiment of FIG. 4. When the metal member of first part 712 is engaged with the magnet of second part 702 to attach surgical drape 710 to patient side cart portion 700, sensor 706 may be an inductive sensor that detects the presence of first part 712 to determine that drape 710 has been attached to patient side cart portion. According to an exemplary embodiment, second part 702 may be a magnet that is axially magnetized, with sensor 706 positioned in a center of second part (such as when second part 702 has a ring shape, as will be discussed below) to minimize interference between the magnetic field of second part 702 and sensor 706.

Although sensor 706 has been described as an inductive sensor, the exemplary embodiments described herein are not limited to an inductive sensor. A sensor to detect the attachment of a surgical drape may be, for example, an optical sensor. An optical sensor may use, for example, light reflected off of first part 712 of drape attachment device or light reflected off of drape 710 itself to detect when drape 710 has been attached to patient side cart portion 700. In another example, an optical sensor may be a sensor that emits a light beam and receives the light beam, but senses the presence of drape 710 when the drape 710 or first part 712 of drape attachment device breaks the beam. A sensor may also be a capacitive sensor that senses a change in capacitance that occurs when a surgical drape has been attached. In another example, a sensor may be a switch that is mechanically depressed or otherwise switched by first part 712 of drape attachment device or drape 710 when the drape is attached.

According to an exemplary embodiment, the surgical system may be configured to provide feedback to a user regarding the installation state of a surgical drape. A surgical system may provide feedback to a user, such as, for example, at a surgeon's console, indicating the installation state of a surgical drape. As a result, personnel may be reminded to install a surgical drape before conducting a surgical procedure to minimize occurrences of surgical drapes not being installed. For example, if a surgical drape has not been installed, the surgical system may provide visual and/or audible feedback indicating the same.

According to an exemplary embodiment, a surgical system may be configured to prevent use of a patient side cart, and any instruments attached to the patient side cart, if the surgical system has not received a signal from the sensor that a drape has been installed on the patient side cart. For example, a surgical system may be configured to lockout use of a patient side cart if signals have not been received for attachment of surgical drapes to one or more arms of a patient side cart, according to an exemplary embodiment. Further, a surgical system may be configured to lockout use of a patient side cart if signals have not been received for attachment of a surgical drape to a main column of a patient side cart, according to an exemplary embodiment. According to another exemplary embodiment, a surgical system may be configured to only require installation of surgical drapes on the arms in order for the patient side cart to be used and only provide feedback regarding the attachment state of a surgical drape to the main column of the patient side cart.

Figure 12:
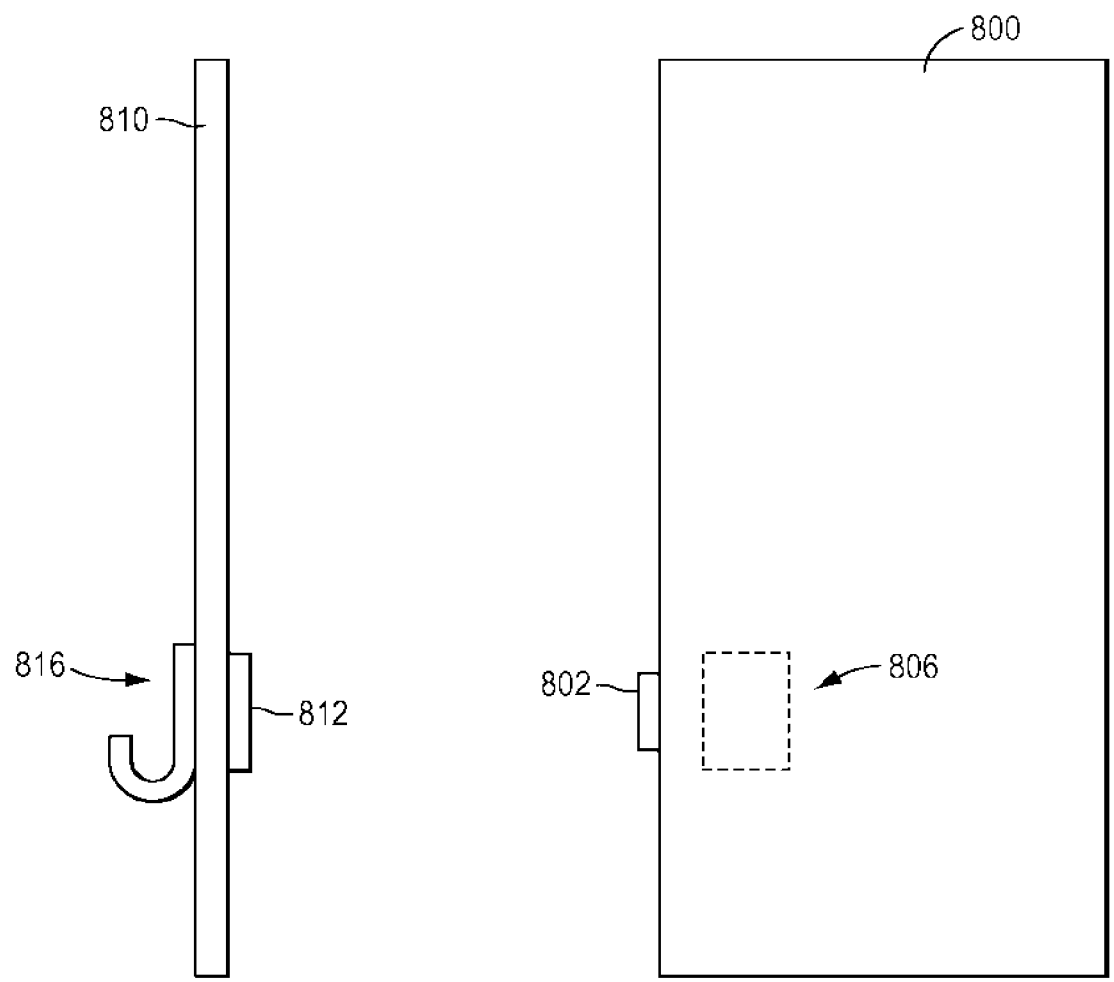
FIG. 12 is a side view of a surgical drape and a portion of a patient side cart in an unattached state, according to an exemplary embodiment.

Although a drape attachment device and a cable support attachment device may be separate devices, as shown in the exemplary embodiments of FIGS. 3, 4, and 9-11, an attachment device may be used that functions as both a drape attachment device and a cable support attachment device, according to an exemplary embodiment. Turning to FIG. 12, a side view is shown of patient side cart portion 800 and surgical drape 810 in an unattached state. Surgical drape 810 includes a first attachment member 812 and patient side cart portion 800 includes a second attachment member 802 configured to engage with first attachment member 812 to attach surgical drape 810 to patient side cart portion 800. First attachment member 812 may be, for example, a metal member and second attachment member 802 may be, for example, a magnet, and patient side cart portion 800 may include a sensor 806 to detect the presence of first attachment member 812 or drape 810, as discussed above with regard to the exemplary embodiment of FIGS. 10 and 11. Surgical drape 810 may further include a cable support 816 connected to first attachment member 812 so that when drape 810 is attached to patient side cart portion 800, cable support 816 is attached to, and supported by, patient side cart portion 800. Thus, the attachment device comprising first attachment member 812 and second attachment member 802 may serve as both a drape attachment member and a cable support attachment member without needed to provide the attachment devices separately.

Figure 13:
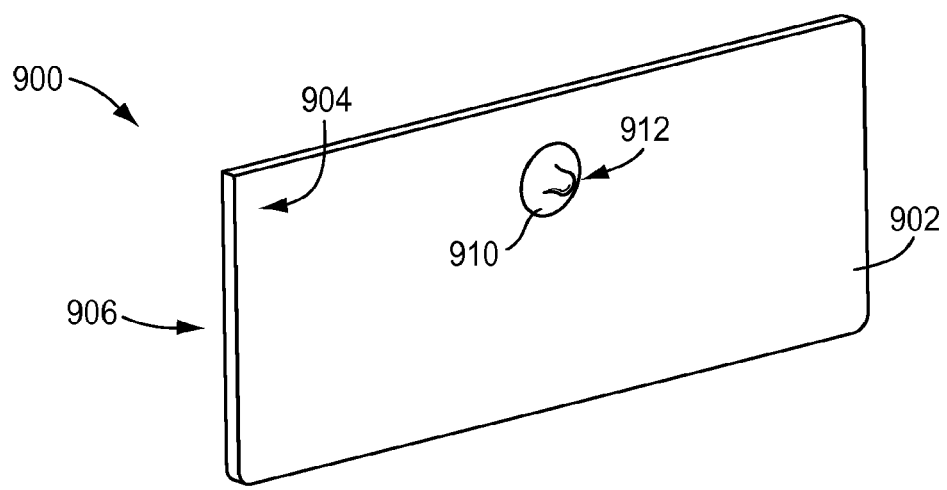
FIG. 13 is a perspective view of a handling member for a drape, according to an exemplary embodiment.

The various exemplary embodiments described above contemplate other arrangements than those described herein. For instance, an attachment device for a surgical drape may be associated with structures other than those described above. Turning to FIG. 13, an exemplary embodiment of a handling member 900 for a surgical drape is shown. Handling member 900 may include a body 902 and a first part 910 of an attachment device. First part 910 of an attachment device may be, for example, a metal member or magnet, as described above in regard to FIG. 3, for attaching a drape. Body 902 may be, for example, a plate structure that provides a larger grasping surface for a user during drape installation than first part 910 alone. Further, due to its size, body 902 may extend the reach of a user when installing and attaching a drape via first part 910. According to an exemplary embodiment, handling member 900 may be located at upper part of drape 340, such as where attachment device 342 is shown in FIG. 2. Thus, when a user is reaching upward to attach drape 340 to main column 304, body 902 extends the reach of the user to make it easier to attach drape 340 to where attachment device 342 is shown. Body 902 may be made of, for example, particle-free cardboard, plastics, metals, or other materials familiar to one of ordinary skill in the art.

Figure 5:
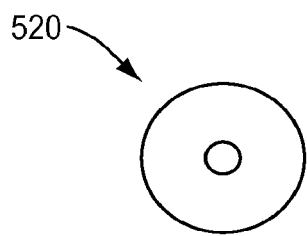
FIG. 5 is a top view of a magnetic attachment, according to an exemplary embodiment.

According to an exemplary embodiment, when first part 910 of handling member 900 comprises a metal member, first part 910 may include a male feature, such as protrusion 912, as shown in FIG. 13. First part 910 and protrusion 912 may be located on a first side 904 that faces and engages a second part of a handling member, such as, for example, a magnet on main column 304, with second side 906 facing the user and away from the main column 304. Protrusion 912 may assist with aligning first part 910 to the second part during attachment, such as when the second part is a ring-shaped magnet, as shown in FIGS. 4 and 5, by inserting protrusion 912 within a female portion, such as a central recess or hole of the ring. Protrusion 912 may also assist with minimizing sliding between first part 910 and the second part during attachment. Further, although protrusion 912 is described with reference to handling member 900, drape attachment devices not including handling member 900 may include a metal member with a male feature, such as first parts 402, 622, 712 and first attachment member 812 of the exemplary embodiments of FIGS. 3 and 9-12.

Figure 14:
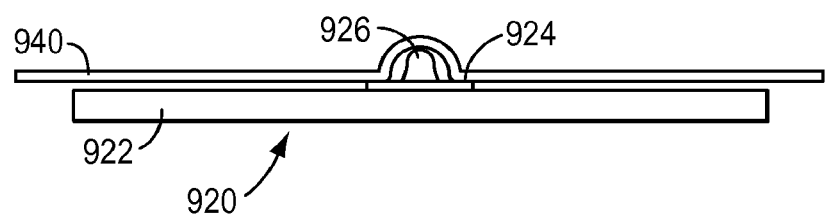
FIG. 14 is a cross-sectional view of a drape attached to a handling member, according to an exemplary embodiment.

Turning to FIG. 14, a side cross-sectional view is shown of an attachment 920 connected to a drape 940. Handling member 920 may be connected to drape 940 by, for example, connecting a first part 924 of an attachment device, including a protrusion 926, to the body 922 of handling member 920 and then attaching drape 940 over first part 924 and body 922. First part 924 may be connected to body 920 by, for example, adhesive bonding, mechanical attachment, and other methods familiar to one of ordinary skill in the art. Drape 940 may be attached to body 920 and first part 924 via, for example, adhesive bonding, mechanical attachment, and other methods familiar to one of ordinary skill in the art.

Figure 15:
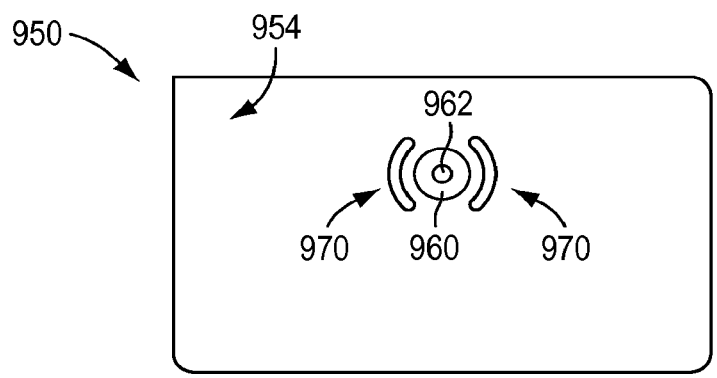
FIG. 15 is a plan view of a handling member including alignment apertures, according to an exemplary embodiment.
Figure 16:
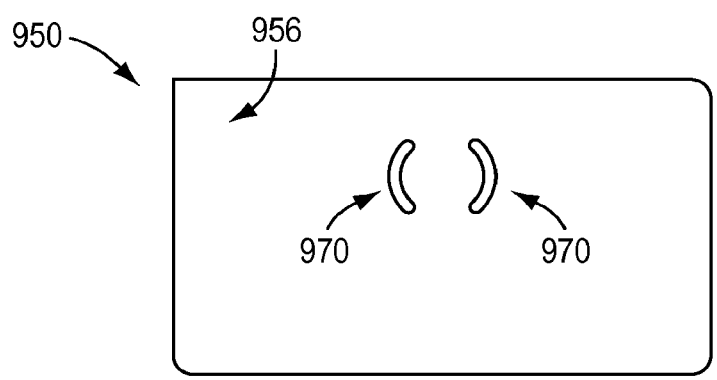
FIG. 16 is a plan view of the handling member of FIG. 15, showing the opposite face of FIG. 15.

The handling member 900 may have other arrangements than those described above for the exemplary embodiment of FIG. 13. Turning to FIG. 15, a handling member 950 is shown from a side that includes a first part 960 of an attachment device, which includes a protrusion 962, similar to that described with respect to handling member 900 of FIG. 13. The side 954 shown in FIG. 15 is the side that faces an object to which handling member 950 is attached, such as, for example, main column 304 in FIG. 2. Because side 954 is facing away from a user during installation of the drape, alignment apertures 970 may be provided in handling member 950. As illustrated in FIG. 16, which shows the side 956 of handling member 950 that faces a user, first part 960 and protrusion 962 may be obscured during drape installation. According to an exemplary embodiment, an object to which handling member 950 is connected, such as main column 304 in FIG. 2, may have an alignment indicator (e.g., a color, pattern, or other visual indicator) with a corresponding shape to alignment apertures 970. Thus, when handling member 950 is being connected to an object, the alignment indicator on the object may be observable through alignment apertures 970 to confirm that handling member 950 is being properly located during attachment of the drape to the portion of the patient side cart.

Figure 17:
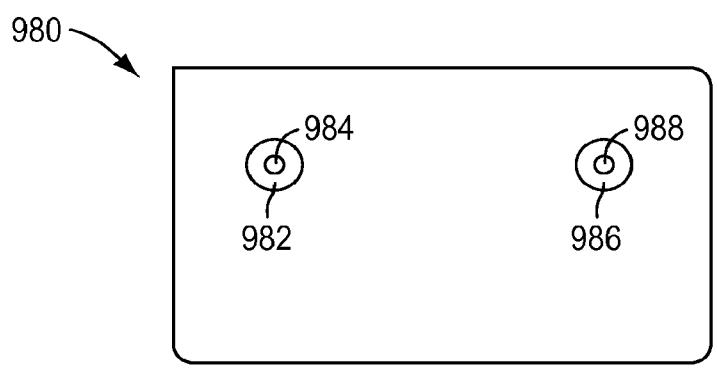
FIG. 17 is a plan view of a handling member including two attachment devices, according to an exemplary embodiment.

A handling member may include more than one attachment device to connect the handling member to an object. Turning to FIG. 17, an exemplary embodiment of a handling member 980 is shown that includes two first parts 982, 986 of two attachment devices, with each including a protrusion 984, 988 to engage with corresponding second parts of attachment devices on a portion of a patient side cart a drape is being installed on. Further, handling members of the exemplary embodiments described herein are not limited to one or two attachment devices and may instead include, for example, three, four, or more attachment devices.

Figure 18:
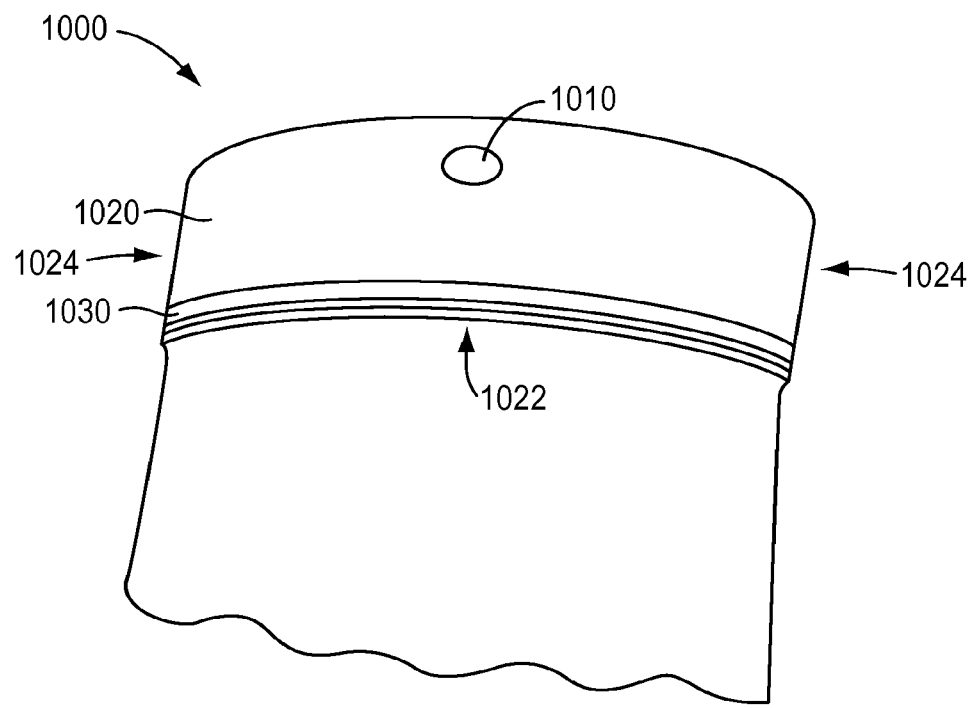
FIG. 18 is a plan view of a drape including a pocket, according to an exemplary embodiment.
Figure 19:
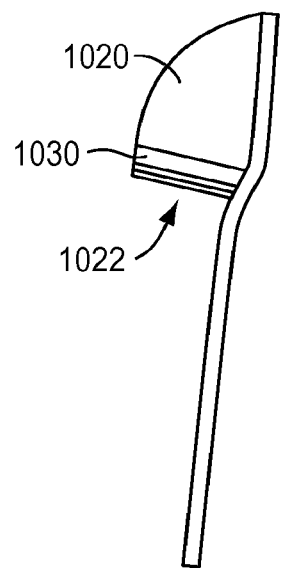
FIG. 19 is a side view of the drape of FIG. 18.

Drapes of various exemplary embodiments described herein may include structures to assist with holding the drape during installation of the drape that facilitate maintaining sterility of the user's hands. Turning to FIG. 18, a drape 1000 is shown that includes a first part 1010 of an attachment device and a pocket 1020. First part 1010 of attachment device may be configured according to first part 402 in the exemplary embodiment of FIG. 3. Pocket 1020 may be formed, for example, by folding a portion of drape 1000 and then bonding 1024 edges of portion to drape 1000, thus forming an opening 1022 for pocket 1020. As shown in FIG. 19, which depicts a side view of drape 1000, a user may insert their hands into pocket 1020 via opening 1022 so that the user may lift drape 1000 without touching the outside of drape 1000, such as at a non-sterile portion of drape 1000. Thus, pocket 1020 may assist with installation of drape 1000 and the user maintaining the sterility of their hands.

To assist a user with identifying sterile areas and non-sterile areas of a drape, a boundary indicator 1030 may be provided to show the boundary between a sterile area and non-sterile area of a drape. Thus, boundary indicator 1030 may indicate where a user may touch a drape, such as to assist a person with sterile hands from touching non-sterile areas of the drape. Boundary indicator 1030 may be, for example, a strip with a color, pattern, or other visual indicator and may be incorporated into a drape via adhesive bonding, printing, molding, or other techniques familiar to one of ordinary skill in the art.

Figure 20:
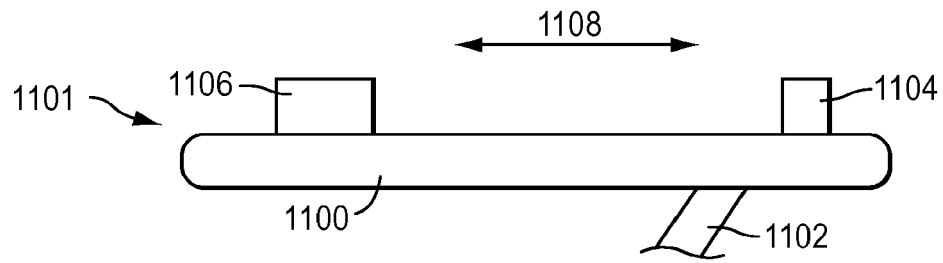
FIG. 20 is a side view of a spar of an arm of a patient side cart, with a carriage on the spar in a retracted position, according to an exemplary embodiment.

Drapes may include features to accommodate moving parts that a drape covers. FIG. 20 shows a side view of a spar 1100 located at an end of an arm 1102 of a patient side cart, such as one of arms 110-113 of FIG. 1. Spar 1100 may include an accessory mount 1104, similar to accessory mount 124 of FIG. 1, and a carriage 1106. Carriage 1106 may include, for example, an actuation interface assembly for attachment of an instrument, similar to actuation interface assembly 122 of FIG. 1, and may be configured to move back and forth along directions 108 on spar 1100 to provide a translation motion for an instrument (not shown), such as, for example, to insert or withdraw the instrument through accessory mount 1104. According to an exemplary embodiment, FIG. 20 shows carriage 1106 in a fully retracted position, while FIG. 21 shows carriage 1106 in a fully inserted position.

Because carriage 1106 moves back and forth under a drape, the drape may be configured to accommodate the movement of carriage 1106. For instance, carriage 1106 may include an instrument sterile adaptor (not shown) to which a drape is attached. However, as carriage 1106 moves along directions 1108, the drape also moves with carriage 1106 due to the attachment of the drape to carriage 1106, such as via attachment of the drape to the instrument sterile adaptor, which is in turn attached to carriage 1106. Thus, the drape must include enough slack and material to permit the drape to both cover spar 1100 and move with carriage 1106, such as when carriage 1106 is moved to the position shown in FIG. 21. However, when carriage 1106 is moved to the fully retracted position shown in FIG. 20, the excess drape material needed to cover spar 1100 (e.g., when carriage 1106 is in the position shown in FIG. 21) may spill off of the end 1101 of spar 1100 as carriage 1106 is retracted and the excess drape material is pushed off of end 1101.

Figure 22:
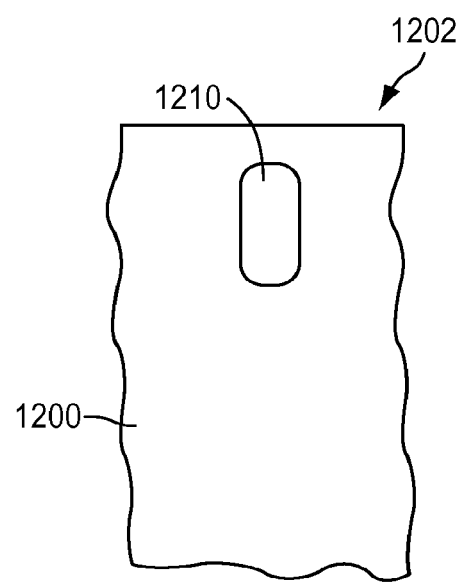
FIG. 22 is top view of a drape including a spar clip, according to an exemplary embodiment.
Figure 23:
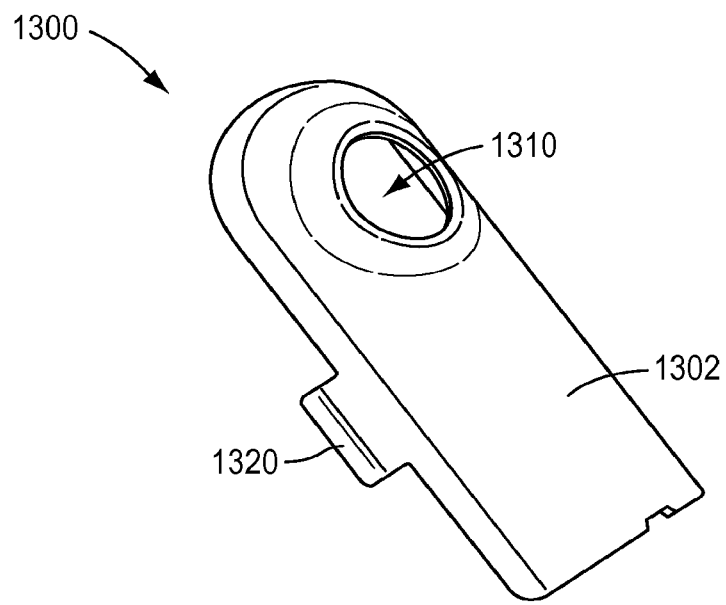
FIG. 23 is a perspective view of a spar clip, according to an exemplary embodiment.
Figure 24:
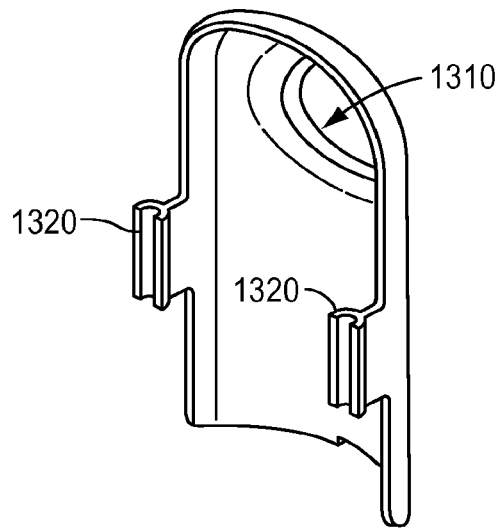
FIG. 24 shows another perspective view of the spar clip of FIG. 23.

A drape may be configured to accommodate for movement of carriage 1106 and excess drape material needed to cover spar 1100. FIG. 22 shows a drape 1200 that includes a spar clip 1210 to attach drape 1200 to a spar. Spar clip 1210 may be attached to an end 1202 of drape 1200 via, for example, thermal welding, adhesive bonding, mechanical attachment, and other techniques familiar to one of ordinary skill in the art. As shown in the exemplary embodiment of FIG. 23, a spar clip 1300 may have a body 1302 with a curved shape, which may correspond to a curved surface of a spar. Spar clip 1300 may further include an aperture 1310, such as to assist with removal of spar clip 1300 from a spar. Spar clip 1300 may further include one or more fasteners 1320, as shown in FIGS. 23 and 24, to connect spar clip 1300 to a spar.

Figure 21:
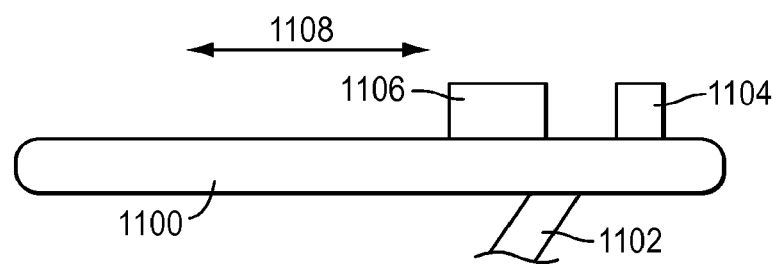
FIG. 21 shows the spar of FIG. 20 with the carriage in an inserted position.
Figure 25:
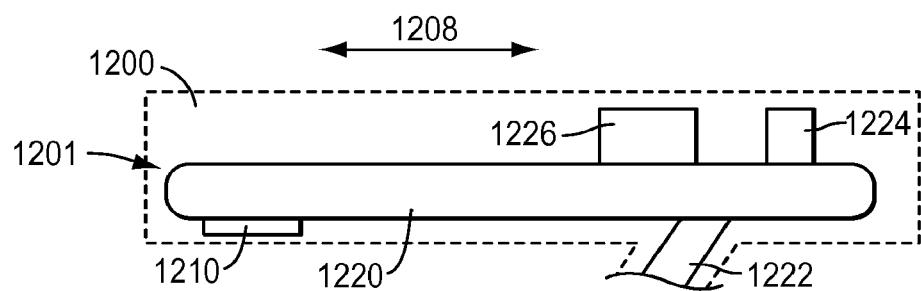
FIG. 25 is a side view of a spar of an arm of a patient side cart covered with a drape, with a carriage on the spar in an inserted position, according to an exemplary embodiment.

Turning to FIG. 25, an exemplary embodiment of a drape 1200 is shown covering a spar 1220 located at an end of an arm 1222, similar to the exemplary embodiment of FIGS. 20 and 21. Drape 1200 may be connected to spar 1220 via a spar clip 1210. Thus, as carriage 1226 moves along spar 1220 in directions 1208, such as towards and away from accessory mount 1224, any excess material of drape 1200 may be prevented from spilling off end 1201 of spar 1220 because the end of drape 1200 is connected to spar 1220 by spar clip 1210. According to an exemplary embodiment, spar end 1201 may be an end of arm 1222.

Figure 26:
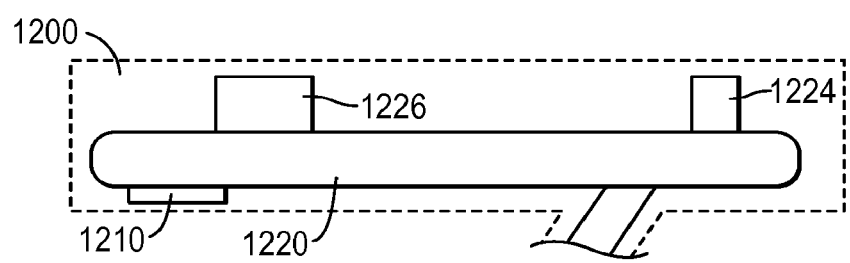
FIG. 26 shows the spar of FIG. 25 with the carriage in a retracted position.

Drape 1200 my fit loosely around carriage 1226, as shown in the exemplary embodiment of FIGS. 25 and 26. According to another exemplary embodiment, drape 1200 may include a pocket (not shown) having a shape corresponding to the shape of carriage 1226 so that drape 1200 fits about carriage 1226. The pocket of drape 1200 may be made of the same material as the remainder of drape 1200, for example. In another example, the pocket of drape 1200 may be made of a different material than the remainder of drape 1200, such as, for example, a LDPE/polyvinyl acetate (PVA) blend, or other drape material discussed above.

Figure 27:
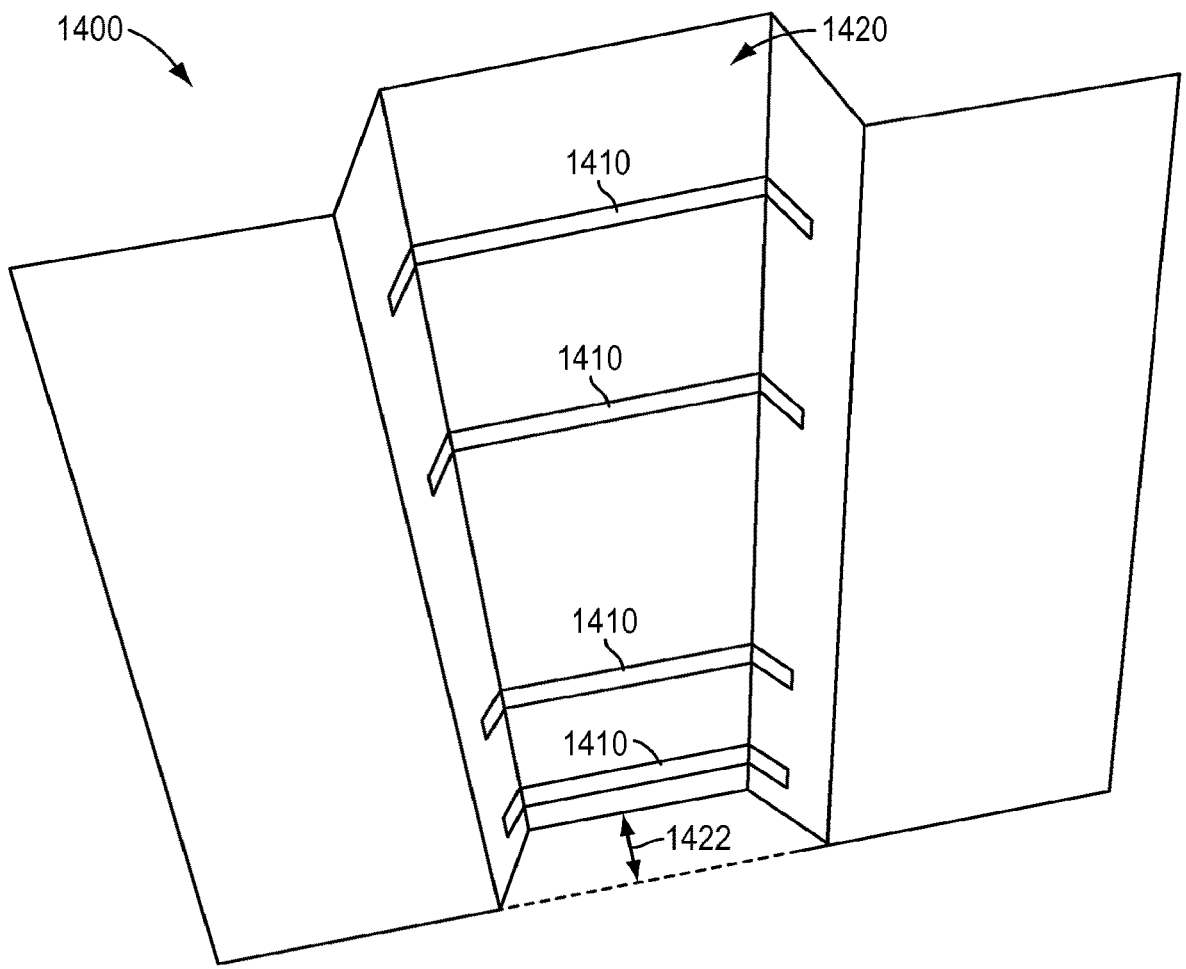
FIG. 27 is a perspective view of a drape including malleable strips forming a channel in the drape, according to an exemplary embodiment.

A drape may also include structures to accommodate the movement of carriage 1106, 1226 to minimize or prevent carriage 1106, 1226 from touching or otherwise snagging the drape as carriage 1106, 1226 is moved. Turning to FIG. 27, an exemplary embodiment of a drape 1400 is shown that includes malleable strips 1410. Instead of using malleable strips 1410 to shape drape 1400 to fit snugly about a spar, such as spar 1220 of the exemplary embodiment of FIGS. 25 and 26, malleable strips 1410 may be used to support drape 1400 into a desired shape that provides a space between drape 1400 and the system portion to which drape 1400 is attached. Thus, malleable strips 1410 may be shaped into support structures that shape drape 1400 into a shape that extends drape 1400 away from an object covered by drape 1400, such as a spar, to provide a space 1420 between drape 1400 and the object. For example, malleable strips 1410 may be deformed to shape drape 1400 so that space 1420 forms a channel through which a carriage may move, such as when carriage 1226 moves along directions 1208 in FIGS. 25 and 26, minimize snagging of drape 1400 by carriage 1226 when carriage 1226 moves. Further, shaping drape 1400 to form space 1420 may facilitate maintaining drape 1400 in a position away from a proximal cannula opening through which an instrument is inserted. Thus, distance 1422 between drape 1400 and an object to which drape 1400 is attached may be approximately the size of carriage 1226.

By providing a surgical drape according to the exemplary embodiments described herein, installation of the surgical drape may be facilitated. For example, the attachment devices described herein permit easy installation and removal of a surgical drape. The surgical drape may include features to facilitate handling of the drape and maintaining a sterile field. A surgical system may be configured to provide feedback that a surgical drape has not been installed because the surgical system may sense whether the drape has been installed. Further, the drape may be configured to be made of various materials providing desirable properties depending on certain applications, such as, for example, abrasion resistance and/or antistatic properties.

Further modifications and alternative embodiments will be apparent to those of ordinary skill in the art in view of the disclosure herein. For example, the devices, systems, and methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents by the following claims.

What is claimed is:

1. A system for providing a sterile barrier for a patient side cart of a teleoperated surgical system, the patient side cart comprising a main column and an arm extending from the main column, the system comprising:
   a drape body;
   a second drape body;
   a pocket on the drape body;
   an attachment device connected to the drape body;
   a second attachment device connected to the second drape body; and
   a rigid coupling member;
   wherein the drape body is sized and shaped to cover at least a portion of the arm;
   wherein the pocket is configured to accommodate a portion of a user's hand in a position external to a sterile boundary defined by the drape body covering at least the portion of the arm;
   wherein the attachment device is removably engageable with a complementary attachment device on the arm;
   wherein the rigid coupling member is configured to attach to the drape body and secure the drape body to the arm;
   wherein the second drape body is configured to cover at least a portion of the main column of the patient side cart; and
   wherein the second attachment device is removably engageable with a second complementary attachment device on the main column.

2. The system of claim 1, wherein:
   the system further comprises a sensor configured to interact with a sensing device such that the sensor senses a state of attachment of the attachment device to the complementary attachment device on the arm.

3. The system of claim 1, wherein:
   the rigid coupling member is configured to attach the drape body to the arm at an instrument actuation interface assembly of the arm.

4. The system of claim 3, wherein:
   the rigid coupling member is a sterile adaptor configured to transmit mechanical input from the instrument actuation interface assembly to an instrument coupled to the instrument actuation interface assembly.

5. The system of claim 1, wherein:
   the rigid coupling member is a spar clip configured to attach to a portion of the arm the portion supporting an instrument carriage.

6. The system of claim 1, wherein:
   the system further comprises a sterile adaptor configured to attach to an instrument actuation interface assembly of the arm and to transmit mechanical input from the instrument actuation interface assembly to an instrument coupled to the instrument actuation interface assembly.

7. The system of claim 1, wherein:
   the attachment device is magnetic.

8. The system of claim 1, wherein:
   the system further comprises a malleable reinforcement member connected to the drape body, the malleable reinforcement member configurable to selectively shape the drape body.

9. The system of claim 1, wherein:
   the drape body comprises a rigid material portion.

10. The system of claim 1, wherein:
    the system further comprises a cable support attached to the drape body and configured to hold and route an instrument cable.

* * * * *